United States Patent
Creger et al.

(10) Patent No.: US 7,695,477 B2
(45) Date of Patent: Apr. 13, 2010

(54) MILLING SYSTEM AND METHODS FOR RESECTING A JOINT ARTICULATION SURFACE

(75) Inventors: Carlyle J. Creger, Logan, UT (US); Daniel F. Justin, Logan, UT (US); E. Marlowe Goble, Logan, UT (US); Robert A. Hodorek, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 802 days.

(21) Appl. No.: 11/138,016

(22) Filed: May 26, 2005

(65) Prior Publication Data
US 2006/0276796 A1 Dec. 7, 2006

(51) Int. Cl.
*A61F 5/00* (2006.01)
(52) U.S. Cl. ...................... 606/87; 606/86 R
(58) Field of Classification Search ........... 606/79, 606/86–89, 96, 179, 180, 170
See application file for complete search history.

(56) References Cited

U.S. PATENT DOCUMENTS

| | | | |
|---|---|---|---|
| 3,748,662 A | 7/1973 | Helfet | |
| 4,719,908 A | 1/1988 | Averill et al. | |
| 4,964,868 A | 10/1990 | Bloebaum | |
| 5,035,699 A | 7/1991 | Coates | |
| 5,037,439 A | 8/1991 | Albrektsson et al. | |
| 5,100,409 A | 3/1992 | Coates et al. | |
| 5,176,684 A | 1/1993 | Ferrante et al. | |
| 5,312,408 A | 5/1994 | Brown | |
| 5,334,205 A | 8/1994 | Chain | |
| 5,344,423 A * | 9/1994 | Dietz et al. ................ 606/87 |
| 5,346,496 A | 9/1994 | Penning | |
| D357,315 S | 4/1995 | Dietz | |
| 5,413,606 A | 5/1995 | Fisk et al. | |
| 5,417,695 A * | 5/1995 | Axelson, Jr. ............... 606/89 |
| 5,474,559 A | 12/1995 | Bertin et al. | |
| 5,484,446 A * | 1/1996 | Burke et al. ............... 606/87 |
| 5,486,180 A * | 1/1996 | Dietz et al. ................ 606/87 |
| D376,202 S | 12/1996 | Burke et al. | |
| 5,609,642 A | 3/1997 | Johnson et al. | |
| 5,634,927 A | 6/1997 | Houston et al. | |
| 5,653,714 A * | 8/1997 | Dietz et al. ................ 606/87 |
| 5,709,689 A | 1/1998 | Ferrante et al. | |
| 5,743,915 A | 4/1998 | Bertin et al. | |

(Continued)

FOREIGN PATENT DOCUMENTS

EP 0 554 959 A1 8/1993

(Continued)

*Primary Examiner*—Thomas C Barrett
*Assistant Examiner*—James L. Swiger
(74) *Attorney, Agent, or Firm*—Baker & Daniels LLP

(57) ABSTRACT

A milling system for use in resecting at least a portion of a joint articulation surface of a bone includes a template having a base with a top surface, an opposing bottom surface, and an opening extending therebetween. One or more fasteners are used to removably mount the template on a bone. A guide is movably mounted on the template and projecting across at least a portion of the opening of the template. The guide is selectively movable across at least a portion of the opening of the template. A rotatable mill is mounted on the guide. The mill is selectively movable along at least a portion of the length of the guide.

37 Claims, 15 Drawing Sheets

U.S. PATENT DOCUMENTS

| | | |
|---|---|---|
| 5,755,803 A | 5/1998 | Haines et al. |
| 5,769,855 A | 6/1998 | Bertin et al. |
| 5,860,981 A | 1/1999 | Bertin et al. |
| 5,885,035 A | 3/1999 | Hoffschneider |
| 5,908,424 A | 6/1999 | Bertin et al. |
| 6,063,091 A | 5/2000 | Lombardo et al. |
| 6,132,468 A | 10/2000 | Mansmann |
| 6,159,216 A | 12/2000 | Burkinshaw et al. |
| 6,355,045 B1 | 3/2002 | Gundlapalli et al. |
| 6,436,101 B1 | 8/2002 | Hamada |
| 6,482,209 B1 | 11/2002 | Engh et al. |
| 6,554,838 B2 | 4/2003 | McGovern et al. |
| 6,620,168 B1 | 9/2003 | Lombardo et al. |
| 6,712,824 B2 | 3/2004 | Millard et al. |
| 6,969,393 B2 | 11/2005 | Pinczewski et al. |
| 2002/0019637 A1 | 2/2002 | Frey et al. |
| 2002/0198528 A1 | 12/2002 | Engh et al. |
| 2003/0028196 A1 | 2/2003 | Bonutti |
| 2003/0130665 A1 | 7/2003 | Pinczewski et al. |
| 2005/0015153 A1 | 1/2005 | Goble et al. |
| 2005/0143745 A1 | 6/2005 | Hodorek et al. |
| 2005/0143831 A1 | 6/2005 | Justin et al. |
| 2005/0192588 A1 | 9/2005 | Garcia |
| 2006/0009776 A1 | 1/2006 | Justin et al. |
| 2006/0009853 A1 | 1/2006 | Justin et al. |
| 2006/0009854 A1 | 1/2006 | Justin |
| 2006/0009855 A1 | 1/2006 | Goble et al. |
| 2006/0167460 A1 | 7/2006 | Pinczewski et al. |
| 2006/0200161 A1 | 9/2006 | Plaskos et al. |
| 2006/0293682 A1 | 12/2006 | Justin et al. |
| 2007/0288029 A1 | 12/2007 | Justin |

FOREIGN PATENT DOCUMENTS

| | | |
|---|---|---|
| EP | 0 502 737 B1 | 9/2002 |
| FR | 2682589 | 4/1993 |
| WO | WO 91/06260 | 5/1991 |
| WO | WO 98/04202 | 2/1998 |
| WO | WO 2004/002332 A1 | 1/2004 |
| WO | WO 2005/069809 A3 | 8/2005 |

* cited by examiner

US 7,695,477 B2

MILLING SYSTEM AND METHODS FOR RESECTING A JOINT ARTICULATION SURFACE

CROSS-REFERENCE TO RELATED APPLICATIONS

Not applicable.

BACKGROUND OF THE INVENTION

1. The Field of the Invention

The present invention relates to milling systems and related guides and mills for resecting at least a portion of a joint articulation surface of a bone and mounting an implant thereat.

2. The Relevant Technology

The human body has a variety of movable orthopedic joints such as the knee joint, hip joint, shoulder joint, and the like. These joints are formed by the intersection of two bones. The intersecting end of each bone has a smooth articular surface that is comprised of articular cartilage. As a result of injury, wear, arthritis, disease or other causes, it is occasionally necessary to replace all or part of an orthopedic joint with an artificial implant. This procedure is referred to as a joint replacement or arthroplasty. For example, a total knee arthroplasty comprises cutting off or resecting the articular surfaces at both the distal end of the femur and the proximal end of the tibia. Complementary artificial implants are then mounted on the distal end of the femur and the proximal end of the tibia. Where only a portion of a joint is damaged, a partial joint arthroplasty can be performed. In this procedure, one or more artificial implants replace only a portion of a joint.

Although joint replacement is now a common procedure that has met with popular success, conventional implants and related mounting techniques have significant shortcomings. One significant drawback of many joint replacements is the extended and painful patient recovery. For example, a traditional knee replacement requires an open procedure wherein a relatively large incision is made which severs a portion of the muscle bounding the femur. The large incision is made so as to fully expose the respective ends of the femur and tibia.

This exposure is necessary when using conventional techniques to resect the femur and tibia and to mount the implants. For example, resecting the femur and tibia is typically accomplished by a reciprocating saw which requires substantially full exposure of the respective ends of the femur and tibia. Furthermore, some conventional tibial implants are screwed directly into the resected end face of the tibia. Mounting such screws again requires substantially full exposure of the resected end face. In yet other embodiments, the implants are formed with posts projecting therefrom. The posts are received within sockets formed on the resected end face of the tibia and femur. Forming of the sockets and inserting the posts into the sockets requires substantially full exposure of the resected end face of the tibia and femur.

Substantially the same procedures are often used when resurfacing only a portion of a joint articulation surface. That is, the joint is exposed and a reciprocating saw is used to resect half or a portion of the articular cartilage. The implant is then mounted by using screws or posts. Thus, even in procedures where only a portion of the joint articulation surface is being resurfaced, conventional procedures make an invasive retraction of the soft tissue and remove a large portion of the bone.

In general, the more invasive the surgery, the more painful, difficult, and time consuming the patient recovery. Furthermore, extensive resection of bone not only increases bone trauma but can also make subsequent replacement operations more difficult.

Accordingly, what is needed are systems and methods for preparing a joint articulation surface to receive an implant which are easy to use while minimizing the impact on soft tissue and the amount of bone resection. What is also needed are implants which can be used with such systems that can be mounted with minimum trauma.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

The present invention relates to milling systems and related guides and mills for use in resecting an articulation surface of an orthopedic joint so that an implant can be mounted on the resected surface. As used in the specification and appended claims, the term "articulation surface" is broadly intended to include all surfaces of natural articular cartilage forming a portion of an orthopedic joint and all articulation wear surfaces of a bone forming a portion of orthopedic joint that, as a result of wear, trauma, disease or other causes, have all or a portion of the natural articular cartilage removed.

In the below illustrated embodiment of the present invention, milling systems and related guides and mills are shown which are specifically designed for mounting a trochlear groove implant at the distal end of a femur. It is appreciated, however, that the illustrated embodiments are simply examples of the present invention and that the same technology can also be used for resecting a portion of the articulation surface at a different location on the same articulation surface or on a variety of other joint surfaces to receive a variety of other different types of implants. By way of example and not by limitation, the present invention can be used for resecting all or a portion of a condyle and then mounting a unicondylar or partial implant. The present invention can also be used for resurfacing an articulation surface of a knee joint, ankle joint, hip joint, shoulder joint, elbow joint, wrist joint, interfrangial joint, or other joints. As such, the milling systems of the present invention can be used for preparing the articulation surface at the proximal or distal end of the femur, tibia, humors, radius, and ulna and on other articulation surfaces of the scapula, pelvis, bones within the foot and hand, and other bone articulation surfaces.

Figure 1:
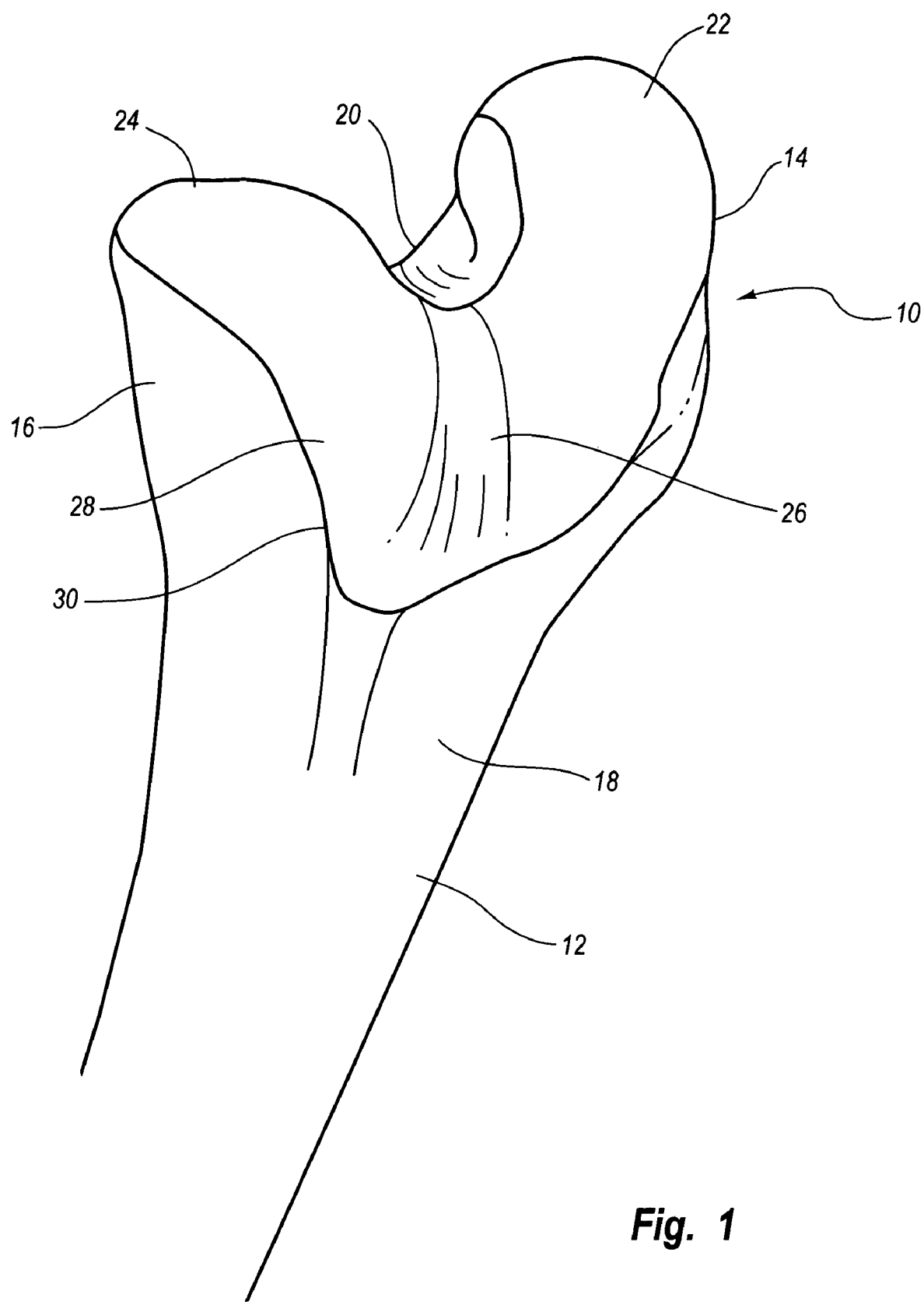
FIG. 1 is a perspective view of the distal end of a femur having a trochlear groove.

Depicted in FIG. 1 is a distal end 10 of a femur 12. Distal end 10 has a medial side 14 and a lateral side 16 that each extend between an anterior side 18 and a posterior side 20. Distal end 10 of femur 12 terminates at a medial condyle 22 and a lateral condyle 24 with a trochlear groove 26 disposed therebetween. Articular cartilage 28 defines an articulation surface for distal end 10 of femur 12. Articular cartilage 28 terminates at a margin 30.

Trochlear groove 26 is a channel that guides the movement of the patella as the knee flexes. On occasion, due to arthritis, disease, trauma, or the like, it is necessary to replace a portion of the femur forming the trochlear groove. In the depicted embodiment of the present invention, the illustrated milling system and related guides and mills are designed to form a recessed pocket on femur 12 at the location of trochlear groove 26 so that an implant can be mounted within the recessed pocket.

Figure 2:
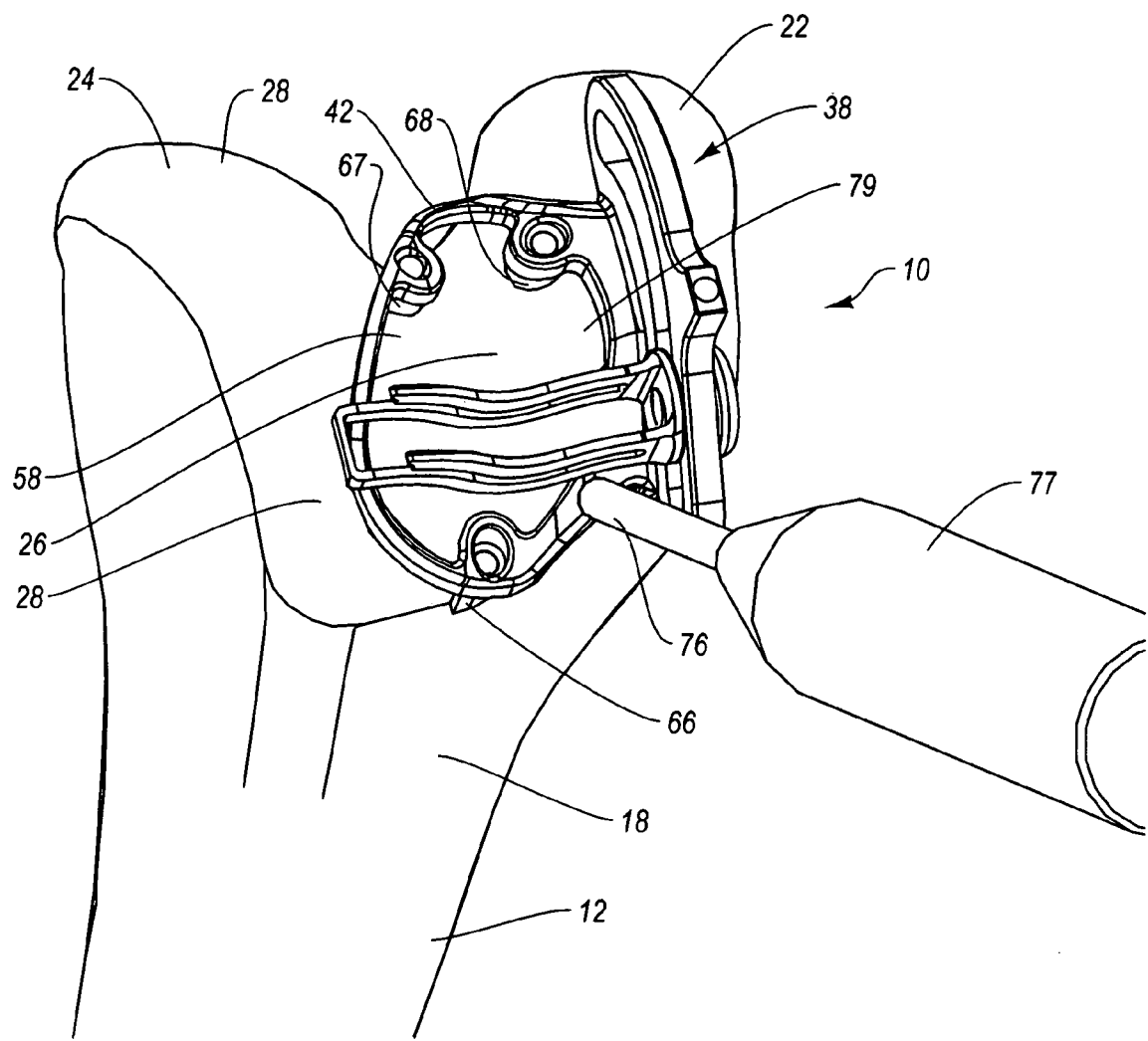
FIG. 2 is a perspective view of a guide system portion of a milling system mounted on the femur of FIG. 1.
Figure 3:
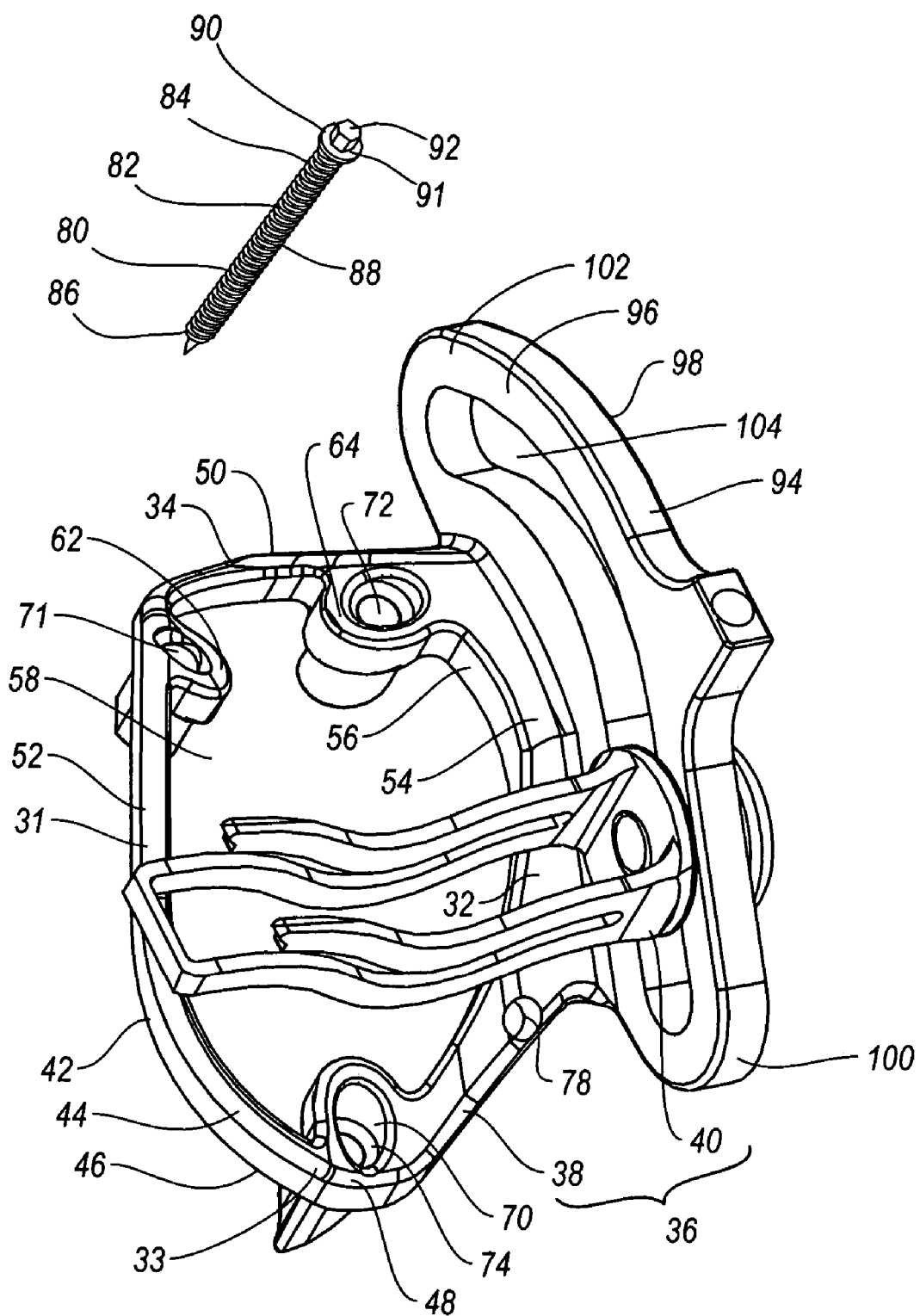
FIG. 3 is a perspective view of the guide system shown in FIG. 2.

Depicted in FIG. 2, is a guide system 36 mounted on distal end 10 of femur 12 over trochlear grove 26. Guide system 36 forms a portion of the milling system. As depicted in FIG. 3, guide system 36 comprises a template 38 having a guide 40 moveably mounted thereon. Template 38 comprises an annular base 42 having a top surface 44 and an opposing bottom surface 46 that each extend between a first end 48 and an opposing second end 50. Surfaces 44 and 46 also extend between a first side 52 and an opposing second side 54. Base 42 can also be defined in terms of having opposing side portions 31 and 32 that extend between a first end portion 33 and an opposing second end portion 34.

Figure 4:
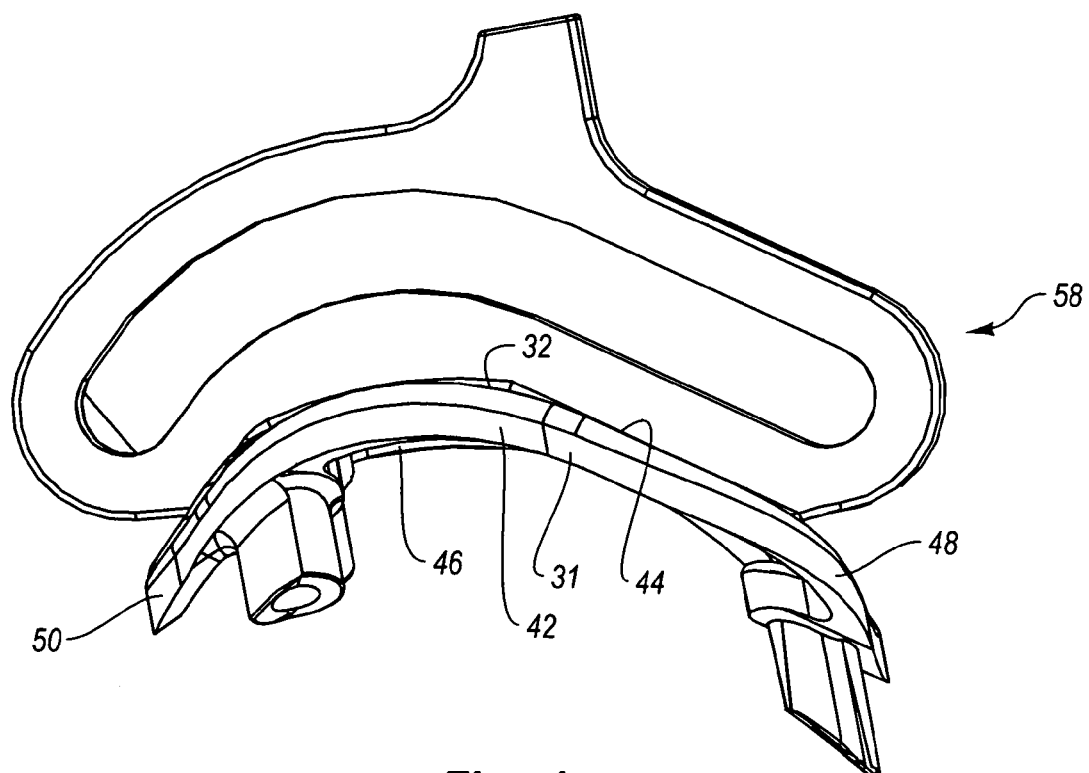
FIG. 4 is an elevated left side view of the guide system shown in FIG. 3.

In one embodiment, as perhaps best depicted in FIG. 4, side portions 31 and 32 of base 42 have a substantially continuous arch extending from first end 48 to opposing second end 50. That is, bottom surface 46 has a substantially constant concave curvature while the top surface 44 has a substantially constant convex curvature. This configuration helps to minimize the size of template 38 to facilitate the greatest ease of insertion during use. In alternative embodiments, however, one or both of top surface 44 and bottom surface 46 can be flat or have any other desired configuration.

Figure 5:
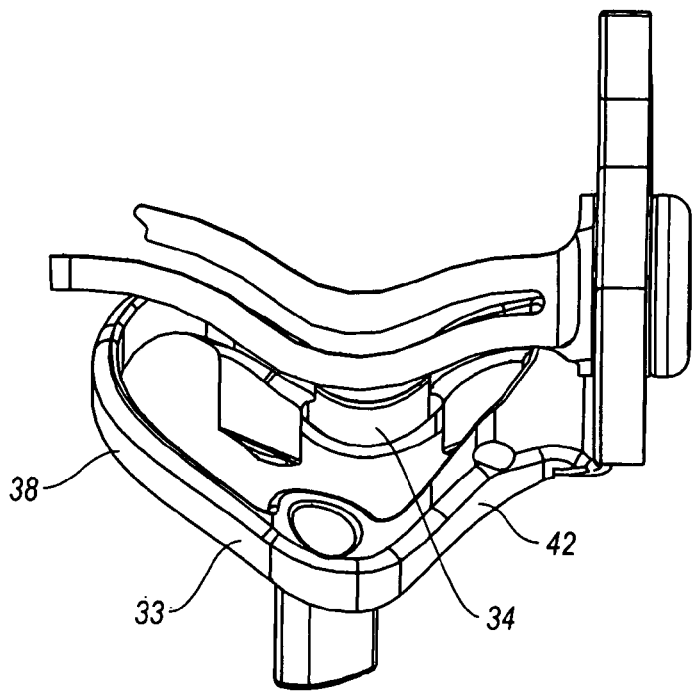
FIG. 5 is an elevated front view of the guide system shown in FIG. 3.

As depicted in FIG. 5, end portions 33 and 34 of base 42 have a substantially V-shaped configuration such that template 38 can sit within trochlear groove 26 (FIG. 1). In alternative embodiments, such as when template 38 is used for mounting a uni- or partial-condylar implant, end portions 33 and 34 need not be V-shaped but can be substantially flat or partially curved. Base 42 is typically designed so as to have a contour complementary to the contour of the portion of the bone over which base 42 sits during use.

Returning to FIG. 3, base 42 also has an interior surface 56 which bounds an opening 58 that extends through base 42 between top surface 44 and bottom surface 46. As will be discussed below in greater detail, opening 58 generally corresponds to the size of the pocket that will be formed on the bone. It is appreciated that opening 58 can have a variety of different sizes and shapes depending on the size and location of the area to be resurfaced. In the embodiment depicted, base 42 completely encircles opening 58. In other embodiments, base 42 can bound only a portion of opening 58.

Figure 6:
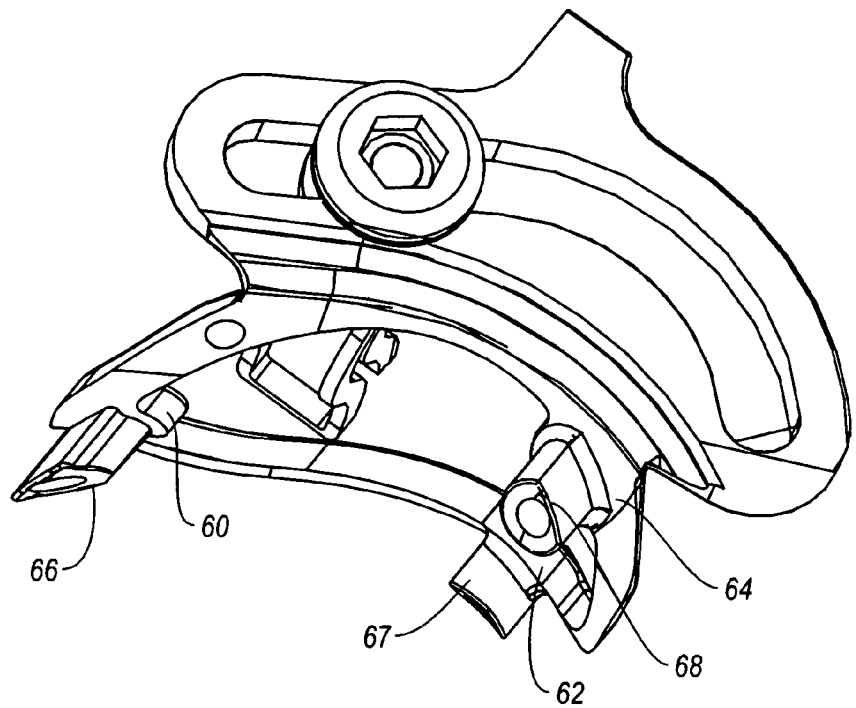
FIG. 6 is a bottom perspective view of the guide system shown in FIG. 3.

A plurality of hubs project from base 42 into opening 58. More specifically, a first hub 60 projects from interior surface 56 of base 42 at first end 48. A second hub 62 projects from interior surface 56 of base 42 at first side 52 of base 42 toward second end 50. Similarly, a third hub 64 projects from interior surface 56 into opening 58 generally at the intersection between second side 54 and second end 50. As depicted in FIG. 6, downwardly projecting from each hub 60, 62, and 64 is a corresponding support leg 66, 67, and 68. As discussed below in greater detail, support legs 66-68 are used to suspend base 42 off of femur 12.

Support legs 66-68 are configured so that base 42 can be placed in a stable orientation spaced above femur 12. Specifically, the area surrounding trochlear groove 26 has an irregular configuration due to the irregular configuration of medial condyle 22, lateral condyle 24, and trochlear groove 26. In contrast to trying to configure base 42 to precisely fit on trochlear groove 26, the use of three support legs 66-68 provides a stable platform that can be easily designed to support base 42 in a stable fashion on a plurality of different sized and shaped femurs.

As depicted in FIG. 2, base 42 is supported on femur 12 as a result of support leg 68 resting against medial condyle 22, support leg 67 resting against lateral condyle 24, and support leg 66 resting against the articular cartilage 28 within trochlear groove 26. In one alternative embodiment base 42 can be sized so that support leg 66 rests against anterior surface 18 outside of articular cartilage 28.

In other embodiments, support legs 66-68 can be positioned at different locations on base 42 and can have a variety of different sizes and shapes. Furthermore, fewer or more support legs can be used. For example, template 38 can be designed with two support legs so that the two support legs and a portion of base 42 rest directly against femur 12. In yet other embodiments, four or more support legs can be formed projecting from body 42. In still other embodiments, the support legs can be eliminated and base 42 mounted directly against articular cartilage 28.

In one embodiment of the present invention, means are provided for removably mounting template 38 onto femur 12 or some other bone. By way of example and not by limitation, extending through each hub 60-62 and each support leg 66-68 is a corresponding mounting hole 70, 71, and 72, as depicted in FIG. 3. Although not required, in the embodiments depicted each mounting hole 70-72 has an annular shoulder 74 that radially, inwardly projects into the corresponding mounting hole at a locating between the opposing ends thereof. Fasteners are designed to pass through mounting holes 70-72 and engage femur 12 so as to secure template 38 to femur 12.

In the depicted embodiment, the fasteners comprise threaded screws 80. Each screw 80 comprises an elongated shaft 82 having a first end 84 and an opposing second end 86. Threads 88 are formed along shaft 82 while an enlarged head 90 is formed at first end 84. In the embodiment depicted, enlarged head 90 comprises a flange 91 that encircles and radially outwardly projects from first end 84. An engagement head 92 extends above flange 91 and has a polygonal or non-circular cross section so that a driver can be connected to engagement head 92 for selective rotation of screws 80.

It is appreciated that enlarged head 90 can be formed with a socket, slot(s), or other engaging surfaces to engage with other types of drivers. Each screw 80 is configured so that second end 86 can be received within and slid through a corresponding mounting hole 70-72 of template 38. Flange 91 is larger than annular shoulder 74 within mounting holes 70-72 so that flange 91 seats against shoulder 74.

One of the benefits of having mounting holes 70-72 extends through support legs 60-62 is that support legs 60-62 function as guides during placement of the fasteners. In alternative embodiments, however, it is appreciated that other numbers of mounting holes and fasteners can be used and that mounting holes 70-72 need not extend through legs 60-62. For example, two mounting holes or four or more mounting holes can be formed through base 42 at locations spaced apart from support legs 60-62. In other alternative embodiments, support legs 60-62 can be eliminated and the fasteners can be used to independently suspend template 38 off of femur 12. In this embodiment, tubular guide sleeves can be passed through the mounting hole to help facilitate alignment of the fasteners. Examples of assemblies that can be used to independently support a template off of a bone are disclosed in U.S. patent application Ser. Nos. 11/040,503, filed Jan. 21, 2005 and Ser. No. 11/083,890, filed Mar. 18, 2005, which are incorporated herein by specific reference. In yet other alternative embodiments, screws 80 can be replaced with other conventional forms of fasteners such as bone anchors, expansion bolts, barbed shafts, and the like.

As also depicted in FIG. 3, template 38 further comprises a bracket 94 that upwardly projects from and extends along the length of second side 54 of base 42. Bracket 94 has an interior face 96 and opposing exterior face 98 that each extend between a first end 100 and an opposing second end 102. An elongated guide slot 104 passes through bracket 94 between faces 96 and 98 and extends between first end 100 and second end 102. In the embodiment depicted, guide slot 104 is arched along the length thereof.

Figure 7:
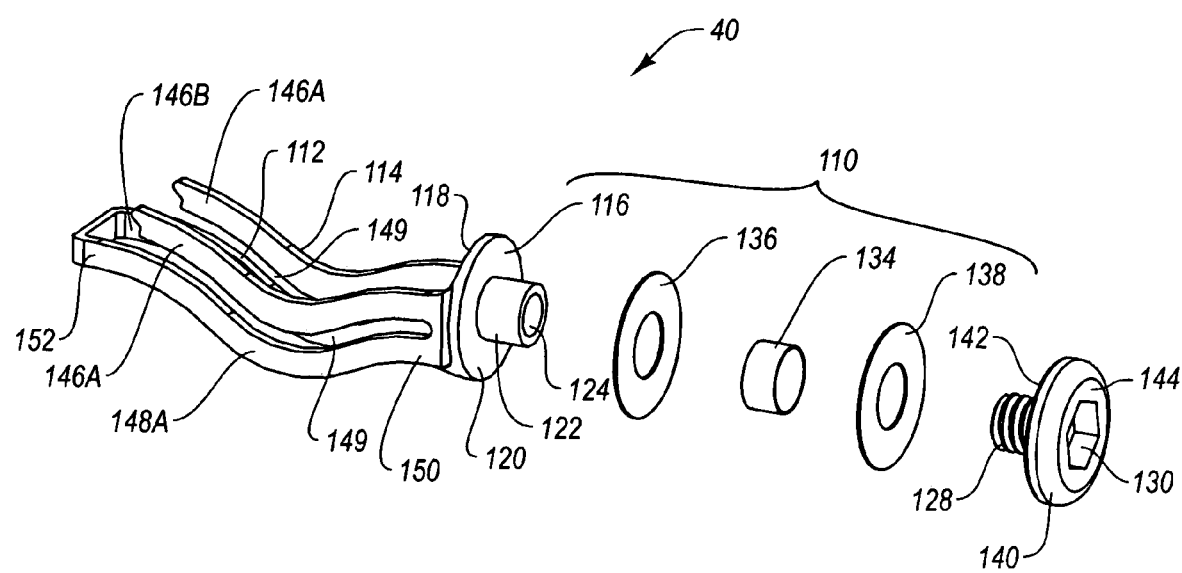
FIG. 7 is an exploded view of the guide of the guide system shown in FIG. 3.

Guide 40 is movably coupled with bracket 94. Specifically, as depicted in FIG. 7, guide 40 comprises a carriage 110 having a pair of spaced apart arms 112 and 114 projecting therefrom. Carriage 110 comprises disc shaped base 116 having an outside face 118 and opposing inside face 120. A tubular stem 122 projects from inside face 120 and is configured to be received within slot 104 of bracket 94. A threaded passage 124 extends into or through stem 122 and base 116. Carriage 110 further includes an enlarged head 140 having an inside face 142 and an opposing outside face 144. A threaded shaft 128 projects from inside face 142 and is configured to threadedly mate with passage 124. A polygonal recess 130 is formed on outside face 144 and is designed to mate with some form of driver. In alternative embodiments, recess 130 can have any desired configuration to mate with other types of drivers.

During assembly, stem 122 is passed into slot 104 of bracket 94 while threaded shaft 128 is threaded into stem 122 from the opposing side of bracket 94. With reference to FIGS. 3 and 7, by threading shaft 128 into stem 122, base 116 and head 140 are fixed on opposing sides of bracket 94 so as to secure carriage 110 to bracket 94. There is sufficient play between carriage 110 and bracket 94 so that carriage 110 can freely slide along the length of guide slot 104 without creating unwanted slop between carriage 110 and bracket 94. To facilitate smooth and easy sliding of guide 40 along guide slot 104, a tubular bearing 134 can be positioned over stem 122 so as to ride against the interior surface of bracket 94 bounding slot 104. Bearing 134 can comprises a sleeve made of low friction material such as Delrin. Other materials or types of bearing, such as ball bearings or roller bearings, can also be used. Furthermore, a thrust bearing 136 can be positioned over stem 122 so as to be disposed between inside face 120 of base 116 and inside face 96 of bracket 94. Likewise, a thrust bearing 138 can be placed over threaded shaft 128 so as to be positioned between inside face 142 of head 140 and outside face 98 of bracket 94. Thrust bearings 136 and 138 can simply comprise washers made of low friction material such as Delrin. Other materials or types of thrust bearings, such as ball or roller thrust bearings, can also be used.

In the embodiment depicted, first arm 112 of guide 40 comprises an elongated upper rail 146A and an elongated lower rail 148A which are spaced apart so as to form an elongated guide slot 149 therebetween. Each rail 146A and 148A has a first end 150 connected to base 116 and an opposing second end 152. Second end 150 of second rail 148A projects farther out than second end 150 of first rail 146A. Second arm 114 is spaced apart from but has substantially the same configuration as first arm 112. As such, second arm 114 also includes an elongated lower rail 146B and a spaced apart, elongated lower rail 148B that each project from base 116 and that have a guide slot 149 formed therebetween. Lower rails 148A and B are connected together at second end 152 thereof.

As depicted in FIG. 2, during initial placement of template 38, a threaded end 76 of an elongated handle 77 is threaded into a threaded hole 78 (FIG. 3) on template 38. Handle 77 can then be used for easy placement and movement of template 38. Other conventional fastening techniques can also be used to removably secure handle 77 to template 38.

Once handle 77 is attached, template 38 is generally aligned by sight and/or feel by placing support leg 68 on medial condyle 22, support leg 67 on lateral condyle 24, and aligning support leg 66 with trochlear groove 26. Furthermore, template 38 is oriented so that opening 58 is disposed over the area that is desired to be resurfaced. The area of articular cartilage 28 disposed within opening 58 is herein referred to as cutting surface 79. Slight adjustments in placement of template 38 can also be made to ensure a stable positioning of template 38. Once template 38 is appropriately positioned, screws 80 or other fasteners are passed through correspondence mounting holes 70-72 on template so as to rigidly fix first template 38 to femur 12. If desired, handle 77 can then be removed from template 38 or retained in place for assisting with removal of template 38.

Figure 8:
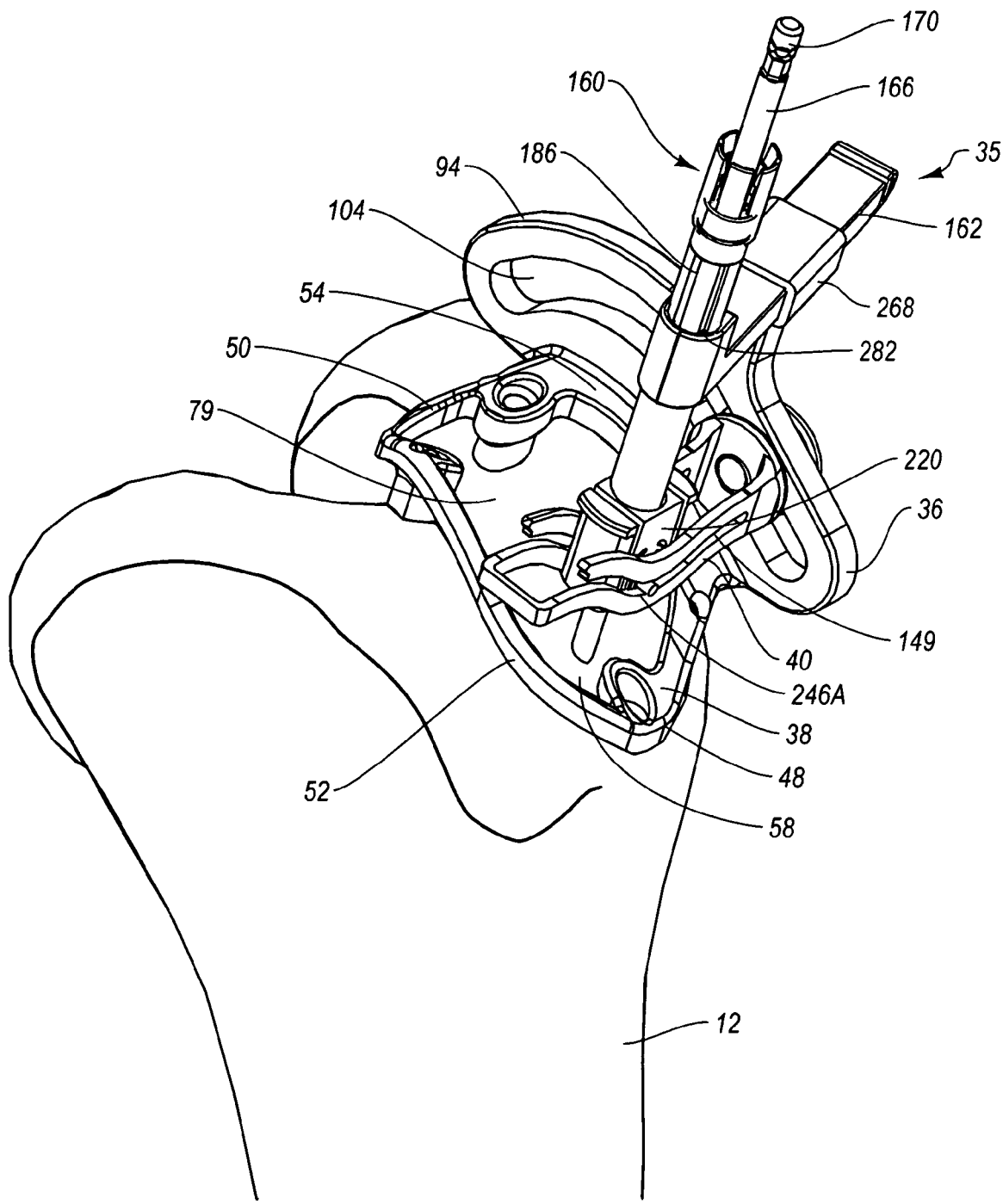
FIG. 8 is a perspective view of the complete milling system mounted on the femur of FIG. 1.
Figure 9:
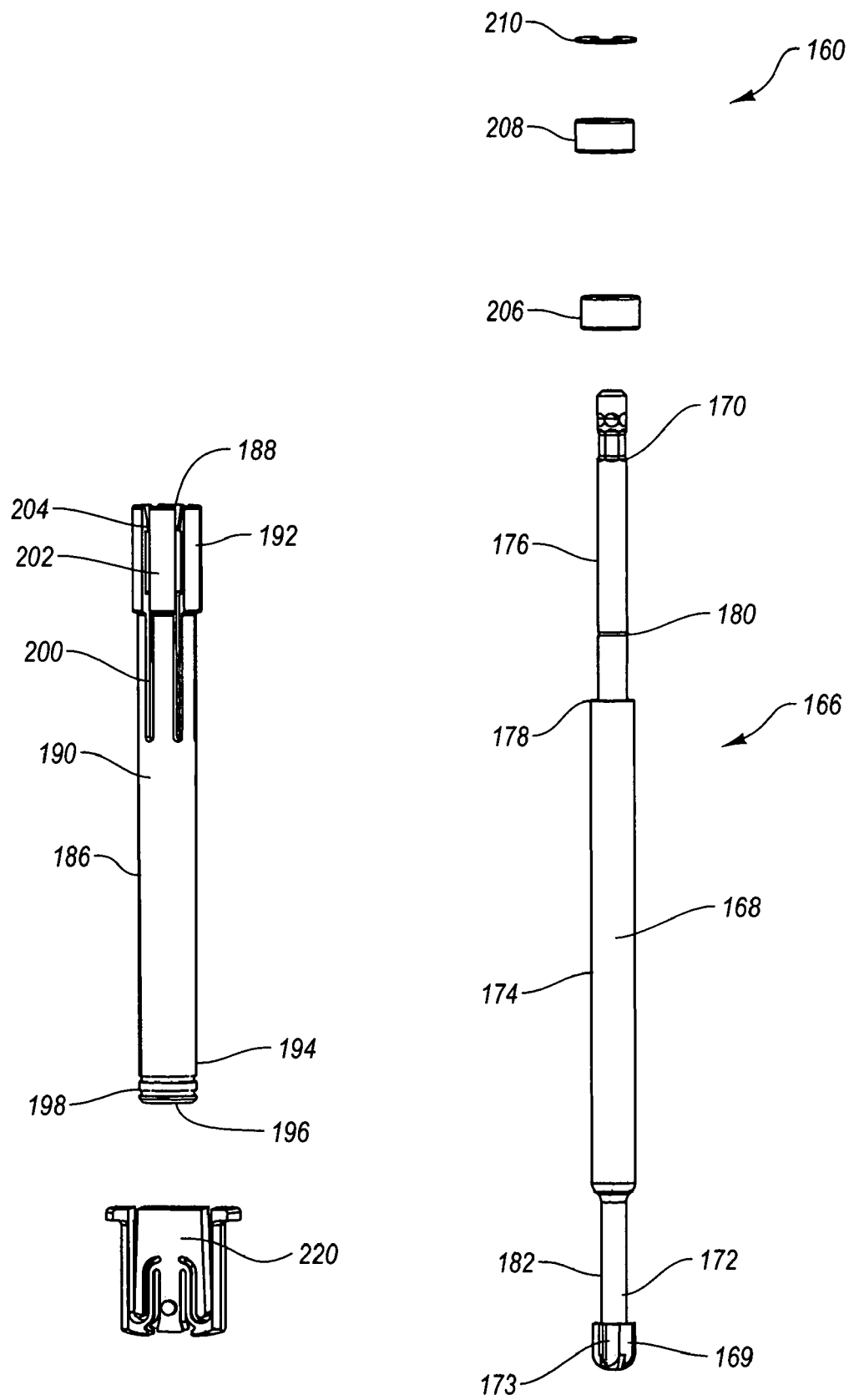
FIG. 9 is a disassembled view of the mill assembly of the milling system shown in FIG. 8.

Turning to FIG. 8, milling system 35 further comprises a mill assembly 160 that is supported by both guide 40 and a brace 162 mounted on template 38. As depicted in FIG. 9, mill assembly 160 comprises a mill 166. Mill 166 comprises a shaft 168 having a burr 169 mounted on the end thereof. Specifically, shaft 168 has a first end 170 and an opposing second end 172. Burr 169 is mounted on second end 172 so as to radially outwardly project from shaft 168. In alternative embodiments the sides of burr 169 can be flush with side of shaft 168. Burr 169 is comprised of a plurality of cutting teeth 173 that enable burr to cut from the side and the bottom. As used in the specification and appended claims, the term "burr" is broadly intended to include any arrangement of cutting teeth or cutting surfaces that when mounted on shaft 168 can be used to cut bone when shaft 168 is rotated. For example, in contrast to having one or more defined cutting teeth, burr 169 can also comprise a roughened surface that can grind or cut away bone.

It is appreciated that shaft 168 can have a variety of different configurations. For reasons as will be discussed below in greater detail, in the depicted embodiment shaft 168 comprises a central portion 174. An engaging portion 176 extends from central portion 174 to first end 170. First end 170 of engaging portion 176 is configured for mating with a drill or other type of driver that can rotatably spin shaft 168. Formed at the junction of central portion 174 and engaging portion 176 is a support shoulder 178. An annular locking slot 180 is recessed on and radially encircles engaging portion 176. Shaft 168 also includes a guide portion 182 extending between central portion 174 and burr 169. Guide portion 182 has a diameter smaller than the maximum diameter of burr 169.

Figure 10:
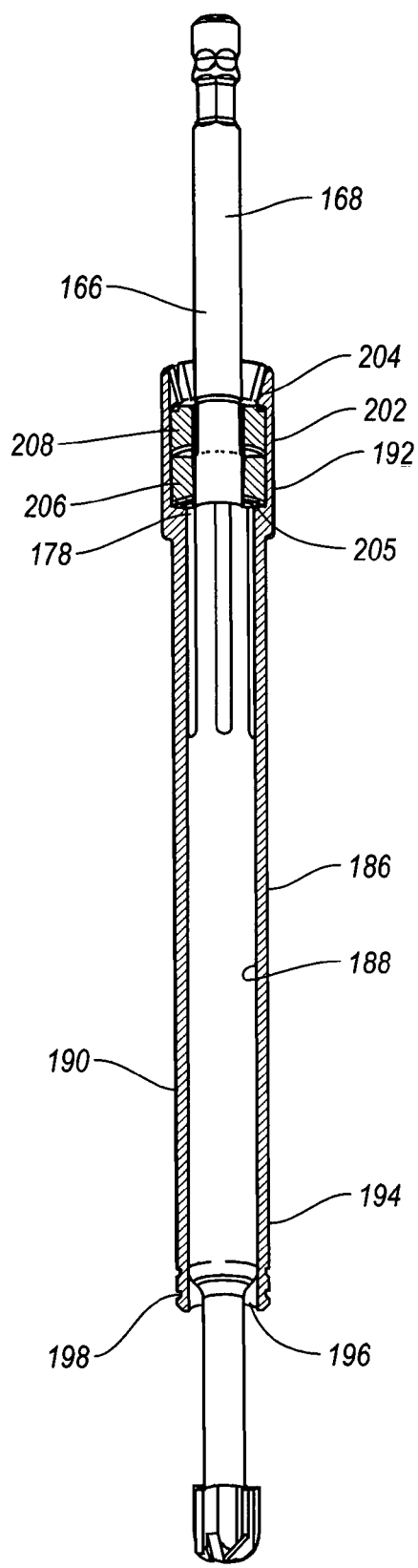
FIG. 10 is a cross sectional side view of the mill assembly shown in FIG. 9.

As depicted in FIGS. 9 and 10, two annular bearings 206 and 208 are selectively passed over first end 170 of shaft 168 so as to sit against support shoulder 178 of shaft 168. Bearings 206 and 208 can be ball bearings, roller bearings, or the like. Alternatively, one or three or more bearings can be used. A clip 210 is then received within locking slot 180 so as to retain bearings 206 and 208 on shaft 168.

Mill assembly 160 also includes a tubular sleeve 186 having an interior surface 188 and an exterior surface 190 each extending between a first end 192 and an opposing second end 194. Interior surface 188 bounds a passage 196 extending through tubular sleeve 186 between opposing ends 192 and 194. Formed on exterior surface 190 at second end 194 are a plurality of annular grooves 198. Grooves 198 encircle tubular sleeve 186 and are spaced apart along the length thereof. In the depicted embodiment, two annular grooves 198 are shown. In alternative embodiments, sleeve 186 can be provided with one annular groove or three or more.

A plurality of slots 200 longitudinally extend through tubular sleeve 186 at first end 192. Slots 200 are radially spaced apart so as to form a plurality of flexible, cantilevered fingers 202. Each finger 202 has a locking barb 204 radially, inwardly projecting from interior surface 188 at first end 192. An annular support shoulder 205 also radially, inwardly projects from interior surface 188 of each finger 202 at a distance spaced apart from barbs 204.

During assembly, second end 172 of shaft 168 is advanced down through opening 196 of sleeve 186 from first end 192. As bearings 206 and 208 first enter passage 196, fingers 202 radially outwardly expand as bearings 206 and 208 pass by locking barbs 204. Once bearings 206 and 208 pass locking barbs 204, fingers 202 resiliently constrict. In turn, bearings 206 and 208 are stopped from further advancing through sleeve 186 by support shoulders 205. As such, bearings 206 and 208 are captured between shoulder 205 and barbs 204, thereby rotatably capturing shaft 168 within tubular sleeve 186.

Figure 11:
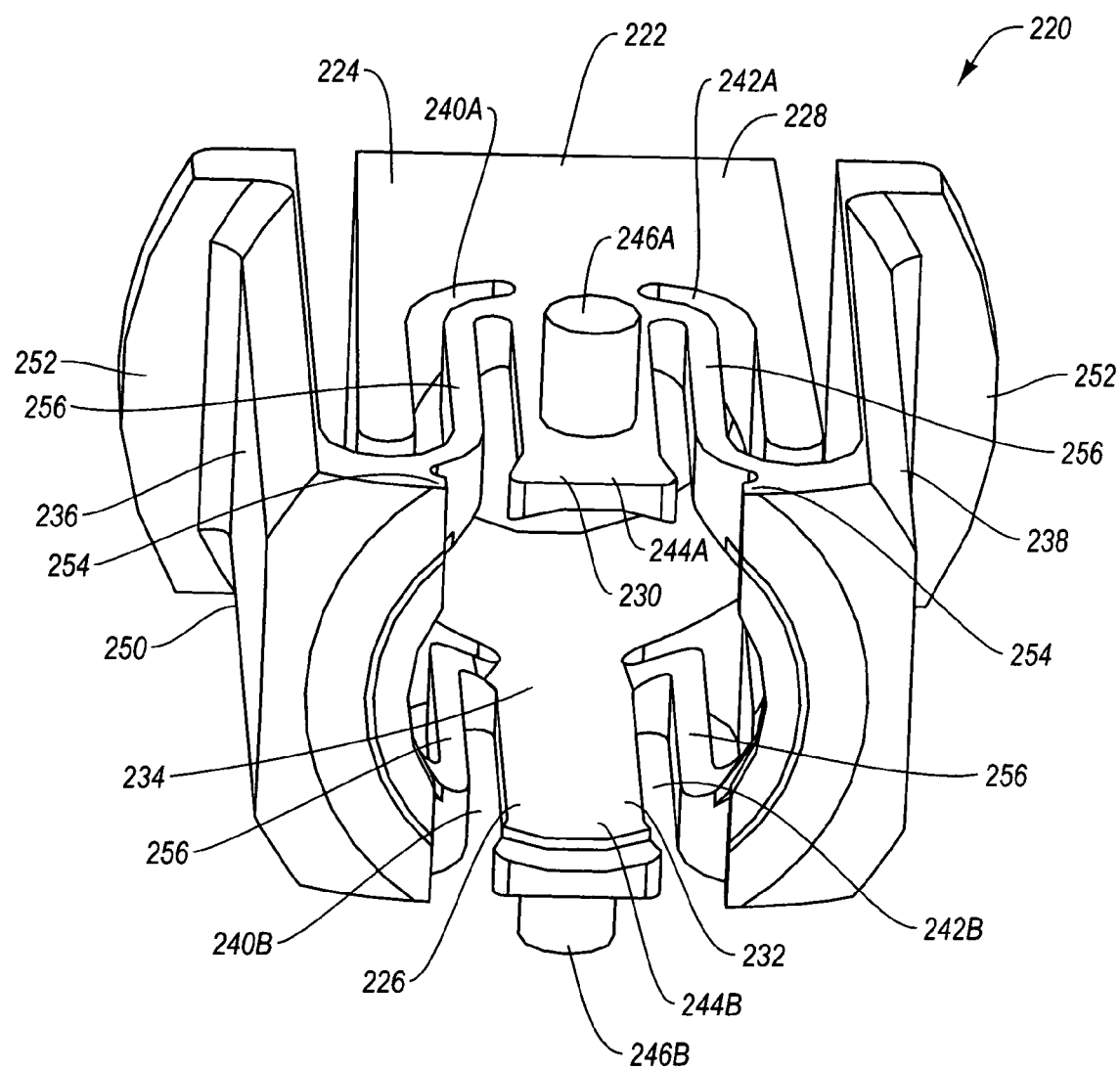
FIG. 11 is a bottom perspective view of the retainer of the mill assembly shown in FIG. 9.

Mill assembly 160 also includes a retainer 220 that is moveably mounted on second end 194 of tubular sleeve 186. As depicted in FIG. 11, retainer 220 comprises a central housing 222 having a front wall 224 and an opposing back wall 226 each extending between a first end 228 and opposing second end 230. Housing 222 has an interior surface 232 which bounds a passageway 234 extending between opposing ends 228 and 230. Front wall 224 and back wall 226 each have a pair of spaced apart slots 240 and 242 that extend therethrough from second end 230. Channels 240A and 242A on front wall 224 bound a tab portion 244A of front wall 224 while channels 240B and 242B on back wall 226 bound a tab portion 244B of back wall 226. As will be discussed below in greater detail, posts 246A and 246B outwardly project from tab portions 244A and 244B, respectively.

Mounted on opposing sides of housing 222 are resilient arms 236 and 238. Each arm 236 and 238 comprises a lever portion 250 having an upper end with a flange 252 outwardly projecting thereat and an opposing lower end with a curved locking ridge 254 radially inwardly projecting thereat. A pair of spaced apart spring rails 256 extends from the lower end of lever portion 250 to an upper end of tab portions 244 within channels 240 and 242. In this configuration, by radially inwardly compressing arms 236 and 238 at flanges 252, locking ridges 254 are radially outwardly separated. In this position, second end 194 of tubular sleeve 186 can be passed down through passage 234 of retainer 220. By releasing arms 236 and 238, spring rails 256 cause locking ridges 254 to resiliently move back towards each other so as to lock within grooves 198 of tubular sleeve 186, thereby securing retainer 220 to tubular sleeve 186. By again compressing arms 236 and 238, tubular sleeve 186 can be moved relative to retainer 220 so that locking ridges 254 can be locked within a different grooves 198, thereby moving tubular sleeve 186 relative to retainer 220.

Figure 12:
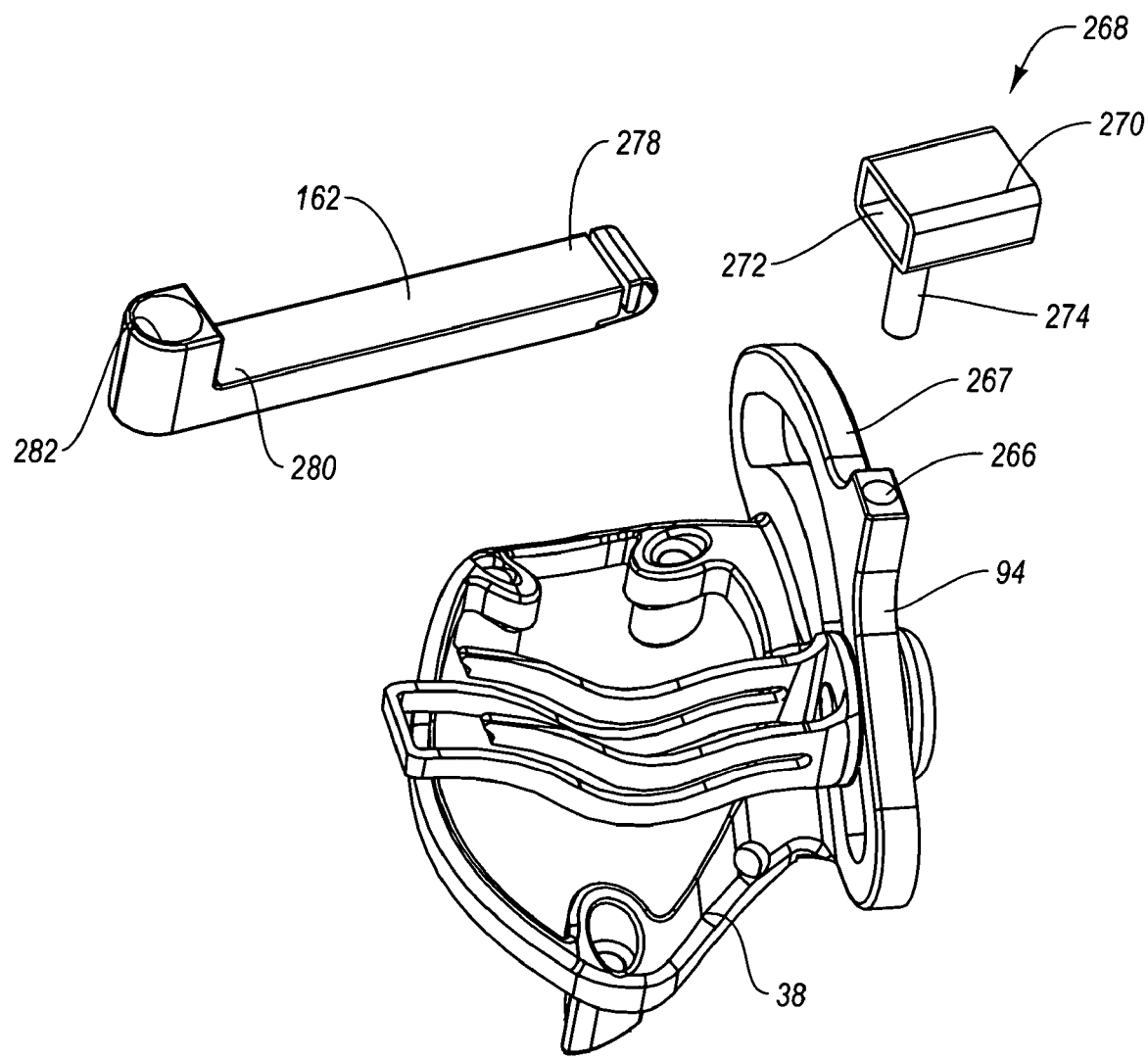
FIG. 12 is a disassembled perspective view of the guide system, brace, and shackle of the milling system shown in FIG. 8.

Turning to FIG. 12, a socket 266 is formed on a top edge 267 of bracket 94 of template 38. A shackle 268 comprises a housing 270 having a channel 272 extending therethrough. A cylindrical post 274 projects from housing 270. During assembly, post 274 is received within socket 266 so that housing 270 can freely rotate about the longitudinal axis of post 274 as post 274 rotates within socket 266. Brace 162 has a first end 278 and opposing second end 280. Brace 162 is slidably disposed within channel 272 of shackle 268. A hole 282 extends through second end 280 of brace 162 and is adapted to receive tubular sleeve 186 therein such that tubular sleeve 186 can freely slide within hole 282.

Returning to FIG. 8, after template 38 is securely attached to femur 12, as previously discussed, mill assembly 160 is coupled with template 38 by coupling with guide 40 and brace 162. Specifically, brace 162 having tubular sleeve 186 slidably extending through hole 282 is slidably positioned within shackle 268. In addition, with retainer 220 coupled with tubular sleeve 186, posts 246A and B of retainer 220 are slidably disposed within corresponding guide slots 149 of guide 40. In this configuration, mill 166 projects down through opening 58 of template 38 so that burr 169 contacts cutting surface 79 of femur 12.

In the assembled configuration, mill assembly 160 is supported by guide 40 and brace 162 at two spaced apart locations along the length of mill assembly 160. This configuration ensures that mill assembly 160 maintains a proper orientation relative to cutting surface 79 as mill 166 is moved along cutting surface 79. Maintaining proper orientation of mill 166 helps ensure that the recessed pocket is formed within precise tolerances.

Once mill assembly 160 is coupled with template 38, a driver (not shown), such as a drill, is coupled with first end 170 of mill 166. By activating the driver, mill 166 rapidly spins within tubular sleeve 186. Spinning burr 169 contacts cutting surface 79 so as to enable resecting of cutting surface 79. It is appreciated that both guide 40 and brace 162 enable mill 166 to move in a controlled three dimensional pattern within opening 58 of template 38. This not only enables mill 166 to operate over the three dimensional profile of cutting surface 79 but is also enables the operator to form the recessed pocket so that the resected surface of the recessed pocket has a desired three dimensional profile that is optimal for receiving an implant.

Specifically, posts 246A and B of retainer 220 travel within guide slots 149 so as to enable mill 166 to travel between opposing sides 52 and 54 of template 38. Although posts 246A and B ride against lower rails 148A and B, upper rails 146A and B help to secure retainer 220 between arms 112 and 114 and help to prevent unwanted tipping of mill 166. The curved contour of guide slots 149 also dictate the vertical travel of mill 166. In turn, guide 40 moves along guide slot 104 of bracket 94 so that mill 166 can move between the opposing ends 48 and 50 of template 38. As such, mill 166 can pass over all of cutting surface 79. Guide portion 182 of the shaft of mill 166 can also ride against and follow along interior surface 56 of template 38 so as to form a clean smooth margin of the resected pocket. It is again appreciated that in this embodiment all horizontal and vertical movement of mill 166 is guided and controlled by the configuration of guide slots 104 and 149.

If desired, the resection of cutting surface 79 can be performed at stages in depth. As a result, burr 169 is not required to cut as much bone in a single pass. For example, during the initial resection, locking ridges 254 of retainer 220 (FIG. 11) can be secured within the lower groove 198 on tubular sleeve 186 (FIG. 9). After the first layer of bone is removed, tubular sleeve 186, and thus mill 166 with burr 169, can be lowered relative to retainer 220 by moving locking ridges 254 into the next higher groove 198 using the method as previously discussed. The milling process can then be repeated to remove the next layer of bone.

During the milling process, brace 162 helps to retain mill 166 in the desired orientation without hampering movement of mill 166. That is, as a result of the fact that brace 162 can freely slide into and out of shackle 268 and can pivot about shackle 268, mill 166 can freely move horizontally within a plane. Furthermore, because tubular sleeve 186 can freely slide vertically within hole 282 of brace 162, mill 166 can also freely move in a vertical orientation. Brace 162, however, prevents tipping of mill 166.

It is appreciated that the milling system of the present invention can have a variety of different configurations and embodiments. By way of example and not by limitation, it is appreciated that guide 40 and retainer 220 function to provide guided movement of mill 166 and that theses structures can have a variety of other designs. For example, upper rails 146A and B can be eliminated; rails 146A and 148A can be combined into a single arm having a recessed groove configured to receive post 246A; arms 112 and 114 can be formed with posts 246 projecting therefrom while recessed slots are formed on retainer 220 to receive posts 246; and posts 246 can project directly from tubular sleeve 186 while arms 112 and 114 could move vertically relative to carriage 110.

In still other embodiments, it is appreciate that there are a variety of conventional, mechanical fastening techniques that can be used and would enable tubular member 186 to move relative to guide 40 and that would enable guide 40 to move relative to bracket 94. In like manner brace 162 can be coupled in a variety of different techniques to bracket 94. For example, in contrast to pivoting, shackle 268 can be slidably mounted on bracket 94. It is also appreciated that the placement of guide 40 and brace 162 can be switched. It is still further appreciate that a variety of different techniques can be used to rotatably secure mill 166 within tubular sleeve 186. For example, the bearings can be press fit between tubular sleeve 186 and mill 166 or a tubular cap can be screwed onto the end of tubular sleeve 186 that replaces locking barbs 204. It is appreciated that numerous other examples also exist for various alternatives of the present invention.

Figure 13:
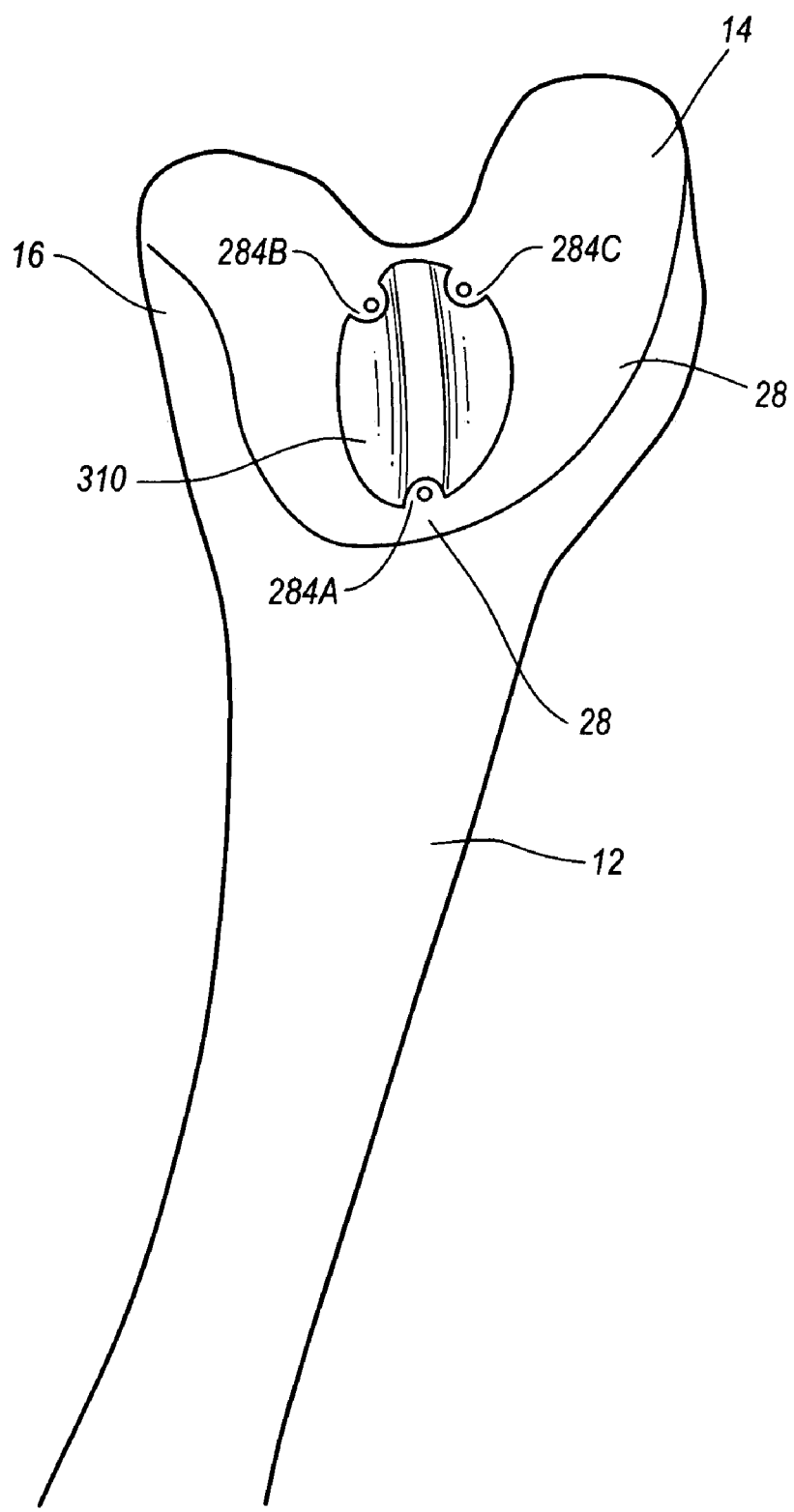
FIG. 13 is a perspective view of the femur shown in FIG. 1 having an incompleted pocket formed thereon by the milling assembly shown in FIG. 8.

Once mill 166 has completed removal of cutting surface 79, milling system 35 is removed from femur 12 so as to expose a partially completed recessed pocket 310. As shown in FIG. 13, protrusions 284A-C of articulation surface 28 that were covered by support legs 66-68 and through which screws 80 extended, project into recessed pocket 310. The surgeon then uses a hand held mill with burr or other cutting apparatus to selectively remove protrusions 284A-C so as to form the final recessed pocket 310, as shown in FIG. 14, in which the implant is ultimately mounted.

This technique has a number of benefits. For example, the only portion of template 38 that contacts articular cartilage 28 are support legs 66-68. It is possible that during the mounting and/or milling process that support legs 66-68 could damage the area of articular cartilage 28 against which support legs 66-68 sit, i.e., protrusions 284A-C. Because protrusions 284A-C are ultimately removed by resection, however, any damage to the surface area of protrusion 284A-C is irrelevant. Furthermore, in this embodiment the holes formed by screws 80 are retained within the final recess pocket 310 and covered by the implant. As such, any potential damage made by the screws is also irrelevant.

Figure 14:
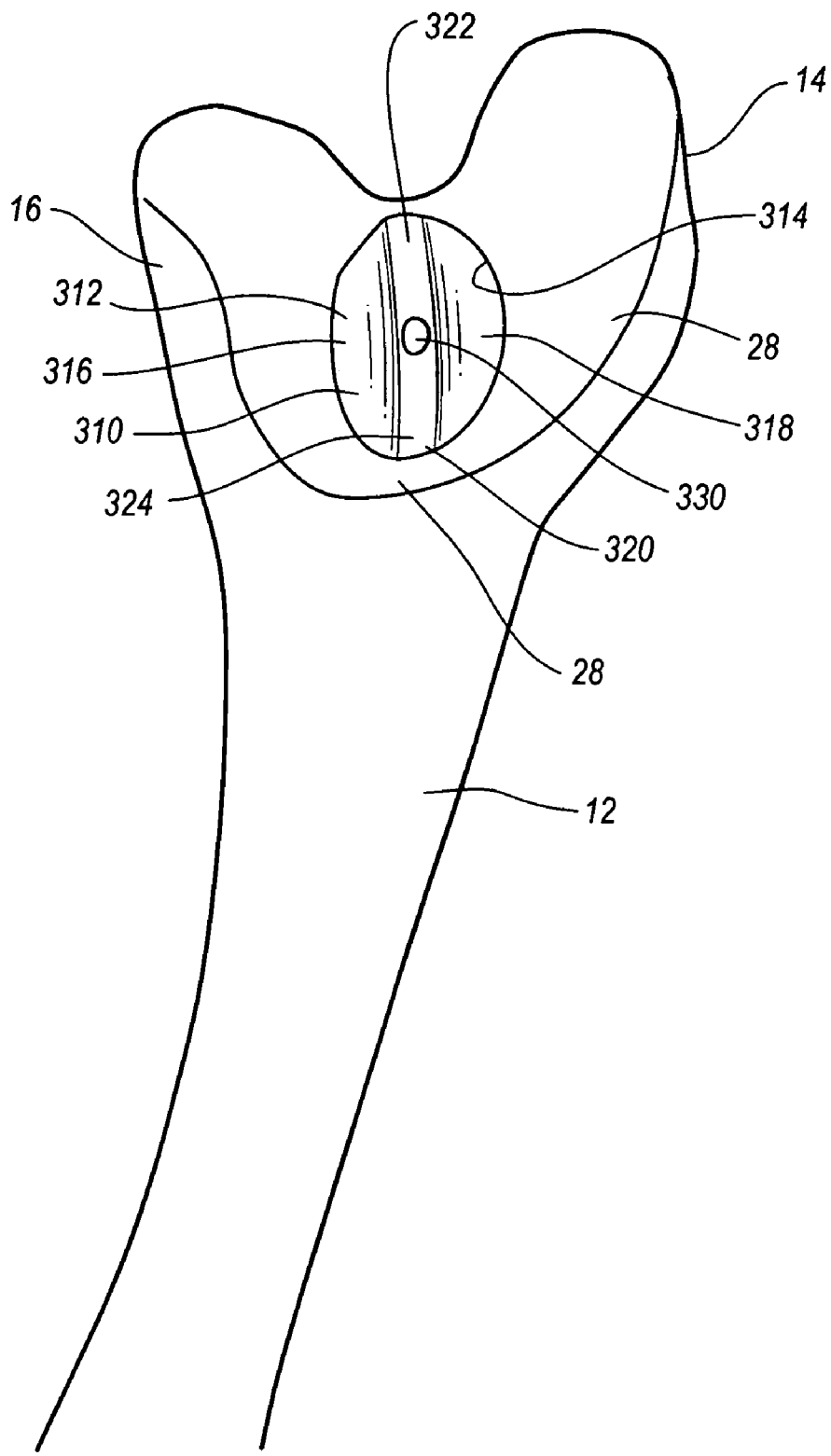
FIG. 14 is a perspective view of the femur shown in FIG. 13 having the completed pocket formed thereon.

As depicted in FIG. 14, pocket 310 is bounded by a floor 312 having an encircling side wall 314 upstanding around the perimeter thereof. Pocket 310 has opposing sides 316 and 318 that extend between a proximal end 320 and an opposing distal end 322. Due to the controlled movement of mill 166, a rounded, elongated channel 324 is recessed along floor 312 in substantial alignment with where trochlear groove 28 was previously disposed. That is, channel 324 extends between opposing ends 320 and 322. Floor 312 also has a convex curvature that extends between opposing ends 320 and 322. As will be discussed below in greater detail, the configuration of recessed pocket 310 enables the formation of a low profile trochlear implant having substantially uniform thickness. Furthermore, the formation of pocket 310 produces a stable platform for the implant having a complementary configuration.

Once recessed pocket 310 is finished, a tunnel 330 is formed extending from pocket 310 to a location spaced apart from the articular cartilage 28, such as medial side 14 or lateral side 16 of femur 12. Tunnel 330 can be formed by simply using a drill to manually form the tunnel. That is, tunnel 330 can be drilled by starting at recessed pocket 310 and extending to the lateral or medial side of the femur 12. Other techniques, guides and instruments for forming tunnel 330 are disclosed in U.S. patent application Ser. No. 10/901,941, filed Jul. 28, 2004 which is incorporated herein by specific reference.

Figure 15:
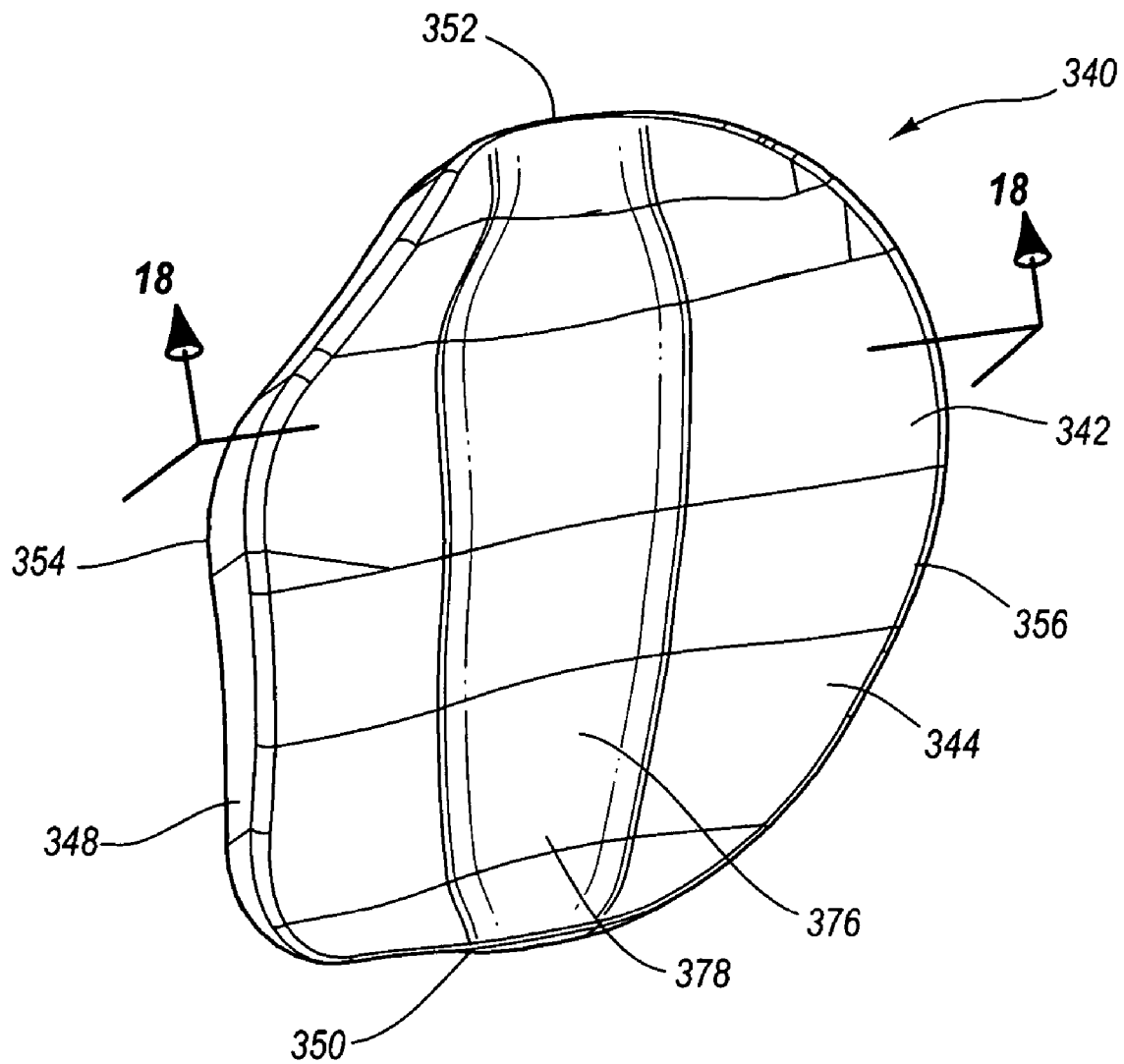
FIG. 15 is a top perspective view of a trochlear implant.
Figure 16:
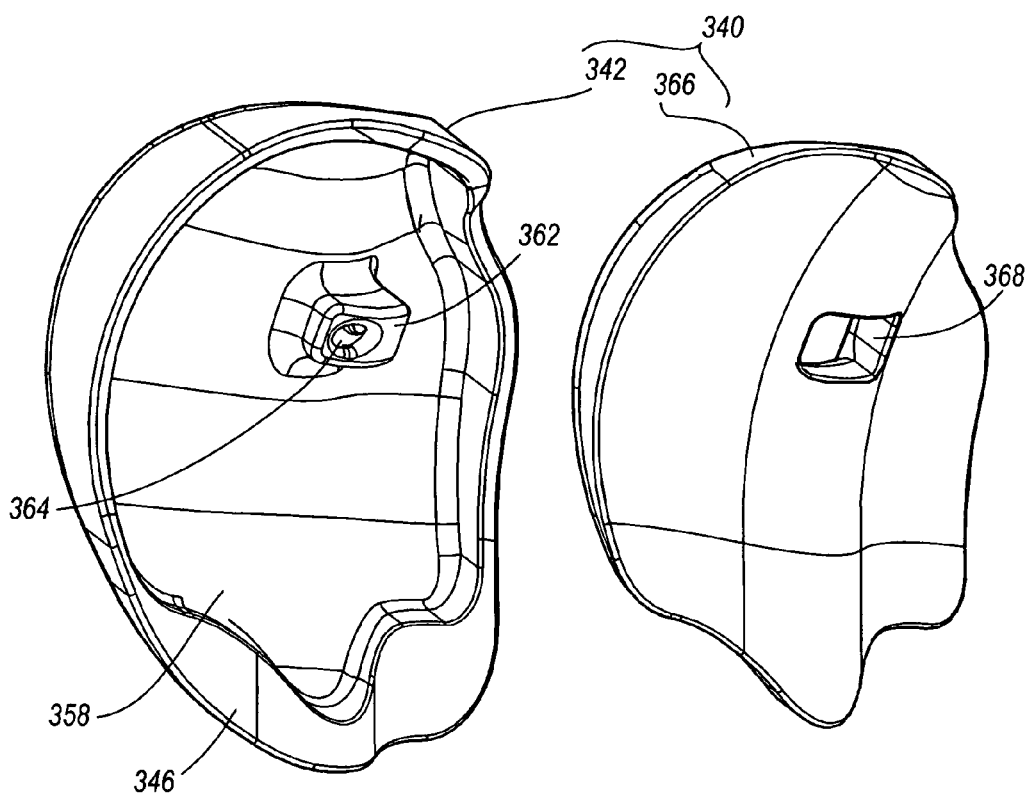
FIG. 16 is a bottom perspective exploded view of the implant shown in FIG. 15.

Once tunnel 330 is formed, a trochlear implant is then secured within the recessed pocket 310. Depicted in FIGS. 15 and 16 is one embodiment of a trochlear implant 340 incorporating features of the present invention. Trochlear implant 340 comprises a body 342 having an articular surface 344 and an opposing bottom surface 346 that each extend to a perimeter edge 348. Body 342 is further defined as having a proximal end 350 and a distal end 352 each extending between a lateral side 354 and a medial side 356. Articular surface 344 is formed having an elongated channel 376 extending between proximal end 350 and distal end 352 substantially centrally between sides 354 and 356. Channel 376 forms at least a portion of the resurfaced trochlear groove in which the patella rides.

Figure 18:
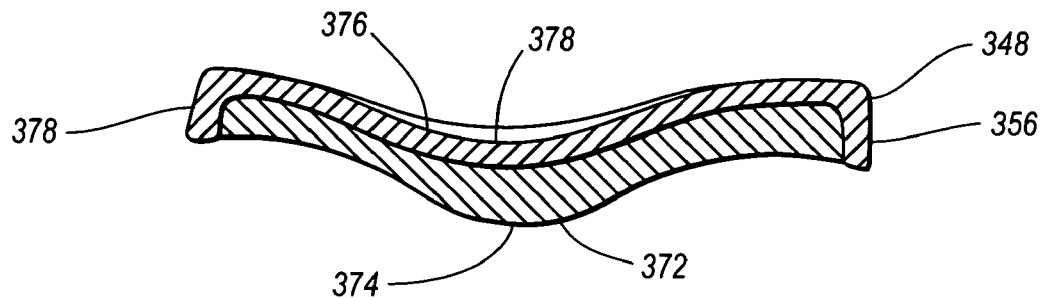
FIG. 18 is a cross sectional side view of the implant shown in FIG. 15 along line 18-18.

In one embodiment viewed in a plane extending between sides 354 and 356 (FIG. 18), channel 376 has a bottom 378 with a concave curvature. The surfaces extending from the concave curvature at bottom 378 to perimeter edge 348 at each side 354 and 356 are typically not concave. Rather, these surfaces are typically substantially flat so as to form a substantially V-shaped transverse cross section with rounded bottom or have a substantially convex curvature. It is also appreciated that articular surface 344 has a smooth continuous convex curvature that extends between opposing ends 350 and 352 (FIG. 15).

Figure 17:
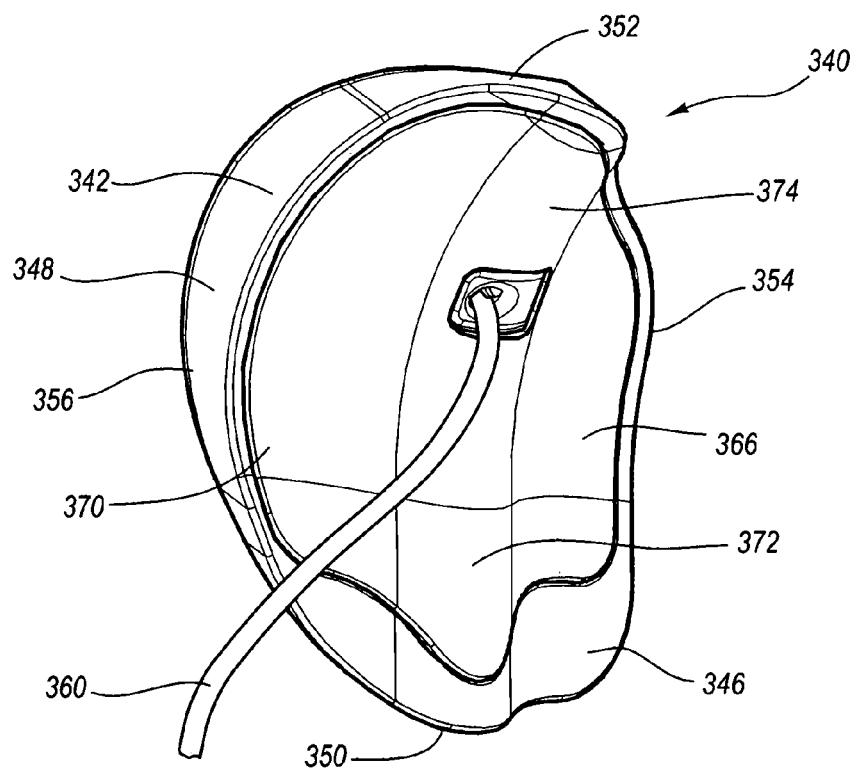
FIG. 17 is a bottom perspective view of the implant shown in FIG. 15 having a line coupled therewith.

Depicted in FIG. 17, a flexible line 360 is secured to trochlear implant 340. As used in the specification and append claims, the term "line" is broadly intended to include wire, cable, cord, suture, braded line, combinations thereof or any other type of flexible filament. The line can be made of metal, alloys, synthetics, composites, or any other desired material. In one embodiment of the present invention the line comprises braded filaments of a cobalt chrome alloy having a diameter in a range between about 0.25 mm to about 5 mm with about 0.5 mm to about 3 mm being more common and about 0.5 mm to about 2 mm being most common. Other dimensions can also be used. The line can be of any desired length.

In one embodiment, the line can also be defined in that for an unsupported length of line of 4 cm, the line has substantially no compressive strength. In yet other embodiments, for an unsupported length of line of 4 cm, the line fails under buckling when an axial compressive load of 0.25 Newtons (N), 1 N, 2 N, 5 N, 20 N, or 50 N is applied. That is, different lines can be used that fail under different loads. Stiffer lines can also be used.

It is also appreciated that the line can be static or resiliently stretchable. In one embodiment where the line is resiliently stretchable, the line can be comprised of a material having shape memory of pseudo elastic properties. One example of such a material is a nickel titanium alloy sold under the name Nitinol. In yet other embodiment, it is appreciated that sections of the line could be replaced with a spring member such as a coiled spring or rubber or bungee type member.

Turning to FIG. 16, formed on bottom surface 346 of body 342 is a pocket 358. In the embodiment depicted, a post 362 projects from within pocket 358. A constricting passage 364 extends through post 362 and is configured to hold flexible line 360. Specifically, line 360 is formed with an enlarged head at one end so that when line 360 is passed through passage 364, the enlarged head is captured within passage 364. Secured within pocket 358 is an inlay 366 of a porous bone ingrowth material. Inlay 366 has an opening 368 formed thereon through which post 362 extends.

Returning to FIG. 17, bottom surface 346 and inlay 366 combine to form a bone apposition surface 370 of trochlear implant 340. Bone apposition surface 370 has a configuration complementary to the formation of recessed pocket 310 formed on femur 12. Bone apposition surface 370 also typically has a configuration complementary to articular surface 344. Specifically, bone apposition surface 370 is formed having a rounded, outwardly projecting ridge 372 that extends between proximal end 350 and distal end 352, substantially centrally between sides 354 and 356. When viewed in a plane extending between sides 354 and 356 (FIG. 18), ridge 372 terminates at an apex 374 having a convex curvature. The side surfaces of ridge 372 extending to sides 354 and 356 are typically substantially flat or have a concave curvature.

Ridge 372 is typically aligned with channel 376 so that trochlear implant 340 can have a substantially uniform thickness. For example, in one embodiment bone apposition surface 370 can be substantially complementary to articular surface 344 so that implant 340 has a substantially uniform thickness between surfaces 344 and 370. In other embodiments, implant 340 may be slightly tapered along perimeter edge 348. Thus, at all locations at least 2 mm in from the perimeter edge 348, body 342 has a thickness extending between the bone apposition surface 370 and the articular surface 344 that does not vary by more than 30%, 20%, or more commonly 15%. Other percentages can also be used. The actual thickness depends on the desired implant and is typically in a range between about 3 mm to about 10 mm.

Ridge 372 is also configured to be complementarily received within channel 324 formed on recessed pocket 310. Bone apposition surface 370 thus also has a continuous concave curvature extending between opposing ends 350 and 352. Because of the unique method in which pocket 310 can be formed, bone apposition surface 370 can be formed having a smooth surface with substantially no stepped shoulders or corners as required in many conventional implants.

Because implant 340 is configured to fit within pocket 310, implant 340 has an outer perimeter having a configuration complementary to pocket 310. It is appreciated that implant 340 as discussed above and depicted herein is only one example of an implant that can be used in association with the present invention. In alternative embodiments, implant 340 can have a variety of different sizes, shapes, configurations, components, and other modifications. For example, spikes or other forms of projections can be formed projecting from bone apposition surface 370. Furthermore, conventional implants using conventional mounting techniques can be secured within pocked 310. Examples of alternative implants that can be used with the present invention are disclosed in the U.S. patent application Ser. No. 10/901,941 which was previously incorporated by reference.

Figure 19:
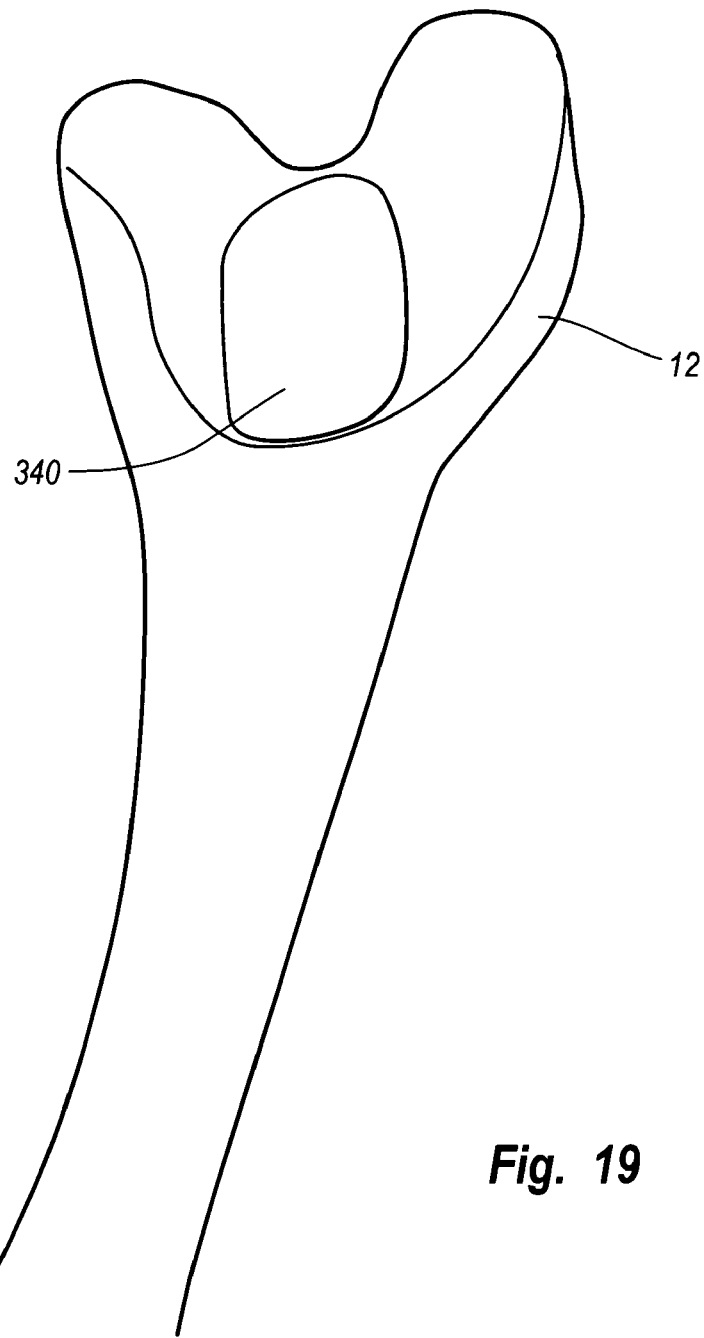
FIG. 19 is a perspective view of the femur shown in FIG. 14 having the implant of FIG. 16 mounted in the pocket thereof.

Finally, turning to FIG. 19, trochlear implant 340 is secured within recessed pocket 310 of femur 12. In the depicted embodiment, this is accomplished by passing line 360 (FIG. 17) within tunnel 330 (FIG. 14) and then using a tensioner and anchor assembly to secure line 360 within tunnel 330. Examples of bone anchors and tensioners that can be used in association with the present invention are disclosed in U.S. patent application Ser. No. 10/901,941. Again, other conventional techniques can be used to secure implant within pocket 360. In such other techniques, line 360 can be eliminated.

The above disclosure discusses a number of different guides, mills and other related instruments, implants and methods. It is appreciated that the individual components and sub-combination of components are novel and can be used independently or mixed and matched with other conventional systems.

Different features of the present invention provide a number of benefits over conventional systems and methods. For example, in contrast to many conventional processes which require the removal of an entire articulation surface for the mounting of an implant, the present invention enables the resurfacing of an isolated location on the articulation surface. As a result, the procedure is less invasive and recovery time is increased. The milling systems of the present invention enable the formation of the pocket while minimizing retraction of soft tissue, minimizing the amount of bone removal, and minimize the time required to remove the bone and mount the implant. Using a high speed burr as opposed to a saw blade or rasp also has advantages in that the burr requires less effort to cut and can more precisely remove sections of bone. Furthermore, unlike saw blades and rasps which during use often cover a portion of the bone which is desired to be removed, burrs allow for greater visibility of the bone during removal, thereby improving accuracy of bone removal.

The milling system is also unique in that the milling system is largely mounted only over the area of the articulation surface that is to be resurfaced. As a result, the potential for unintentional damage to the portion of the surrounding articular surface that is not to be resurfaced is minimized. Another advantage of the present invention is that it provides a system that is easy to mount and use on uneven or irregular surfaces, is easy to operate, and is easy to remove. The present invention also provides other advantages which will be apparent to those skilled in the art.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A milling system for use in resecting at least a portion of a joint articulation surface of a bone, the system comprising:
    a template comprising:
        a base having a top surface and an opposing bottom surface both extending from a first end to a spaced apart second end, the base including an opening extending between the top and bottom surfaces, at least two support legs projecting from the base so as to project below the bottom surface, the at least two support legs being interposed between the bottom surface of the base and a bone when the template is mounted to the bone;
        a bracket upwardly projecting from the base, the bracket having an elongated guide slot extending from the first end to the second end of the base;
    means for removably mounting the template on the bone when the at least two support legs are resting on the bone so as to suspend the bottom surface of the base of the template above the bone;
    an elongated guide mounted to the bracket and projecting across at least a portion of the opening of the template, the guide being mounted to the bracket so that the guide can be selectively moved along the guide slot and can be rigidly fixed to the bracket at different locations along the guide slot, and
    a rotatable mill movably engaged with the guide so as to be selectively movable within the opening of the template.

2. The milling system as recited in claim 1, wherein the at least two support legs comprise at least three spaced apart support legs projecting from the bottom surface of the base so that the support legs can independently support the base off of a surface.

3. The milling system as recited in claim 2, wherein the means for removably mounting comprises:
    at least three spaced apart mounting holes formed on the template, each mounting hole extending through a corresponding one of the support legs; and
    at least three fasteners, each fastener being adapted to pass through a corresponding one of the mounting holes and engage the bone.

4. The milling system as recited in claim 1, wherein the at least two support legs are integrally formed with or permanently attached to the base.

5. The milling system as recited in claim 1, wherein a portion of the base has a substantially V-shaped contour.

6. The milling system as recited in claim 1, wherein the means for removably mounting comprises at least one mounting hole formed on the template and a fastener adapted to pass through the at least one mounting hole and engage the bone.

7. The milling system as recited in claim 6, wherein the base comprises:
    an annular ring that encircles the opening; and
    at least three spaced apart hubs projecting from the annular ring into the opening, each hub having a corresponding mounting hole extending therethrough.

8. The milling system as recited in claim 1, further comprising:
    a retainer slidably coupled with the guide; and
    a tubular sleeve having a passage extending therethrough, the tubular sleeve being coupled with the retainer, the mill being rotatably disposed within the tubular sleeve.

9. The milling system as recited in claim 1, wherein the bracket upwardly projects from a side of the base.

10. The milling system as recited in claim 1, wherein the guide includes a pair of spaced apart arms configured to receive the mill therebetween.

11. The milling system as recited in claim 1, wherein the guide has an elongated guide path extending along the length thereof, the rotatable mill being movable along the guide path, the guide path curving in two dimensions so that when the opening formed on the template is horizontally disposed, the guide path curves vertically in two dimensions above of the opening.

12. A milling system for use in resecting at least a portion of a joint articulation surface of a bone, the system comprising:
    a template comprising a base having a top surface and an opposing bottom surface both extending from a first end to a spaced apart second end and from a first side to a spaced apart second side, the base including an opening extending between the top and bottom surfaces;
    means for removably mounting the template on a bone;
    a guide extending between a first end and a spaced apart second end, the guide being mounted on the template and projecting between the first and second sides of the template across the opening of the template, the entire guide being movable between the first end of the template and the second end of the template while the guide is coupled to the template; and
    a rotatable mill mounted on the guide, the mill being selectively movable at least substantially between the first and second sides of the template while mounted on the guide.

13. The milling system as recited in claim 12, further comprising at least two spaced apart support legs projecting from the base so as to extend below the bottom surface.

14. The milling system as recited in claim 12, wherein the means for removably mounting comprises:
    at least three spaced apart mounting holes formed on the template; and
    at least three fasteners, each fastener being adapted to pass through a corresponding one of the mounting holes and engage the bone.

15. The milling system as recited in claim 12, wherein the template further comprises a bracket projecting from the base and extending along the length of the opening of the template, the guide being coupled with and selectively movable along the length of the bracket.

16. The milling system as recited in claim 15, wherein the guide comprises a carriage coupled with the bracket and a pair of spaced apart arms projecting from the carriage and across at least a portion of the opening of the template.

17. The milling system as recited in claim 16, further comprising:
    a retainer having a tubular sleeve coupled therewith, the mill being disposed within the tubular sleeve; and means for coupling the retainer to the guide so that the retainer can selectively move along the length of the guide between the first and second sides of the template.

18. The milling system as recited in claim 17, wherein the means for coupling comprises:
   each arm of the guide having a slot formed along the length thereof; and
   a post projecting from each side of the retainer, the retainer being disposed between the arms of the guide with each post being slidably disposed within the slot of a corresponding arm.

19. The milling system as recited in claim 12, further comprising a brace movably mounted on the template so as to extend over a portion of the opening of the template, the mill being supported by the brace.

20. The milling system as recited in claim 19, further comprising a tubular sleeve having a passage extending therethrough, the mill being rotatably disposed within the tubular sleeve, the tubular sleeve being coupled with the brace.

21. The milling system as recited in claim 12, wherein the guide has an elongated guide path extending along the length thereof, the rotatable mill being movable along the guide path, the guide path curving in two dimensions so that when the opening formed on the template is horizontally disposed, the guide path curves vertically in two dimensions above of the opening.

22. A milling system for use in resecting at least a portion of a joint articulation surface of a bone, the system comprising:
   a template comprising a base having a top surface and an opposing bottom surface with an opening extending therebetween, the base also having a first end and an opposing second end with the opening positioned therebetween;
   means for removably mounting the template on a bone;
   a guide mounted to the template and projecting across the opening of the template, the entire guide being movable from the first end of the base to the second end of the base while the guide is mounted to the template;
   a brace movably mounted on the template so as to extend over a portion of the opening of the template, the brace being spaced apart from the guide; and
   a rotatable mill supported by the brace and the guide, at least a portion of the mill being disposed within the opening of the template.

23. The milling system as recited in claim 22, further comprising at least two spaced apart support legs projecting from the base so as to extend below the bottom surface of the base.

24. The milling system as recited in claim 22, wherein the means for removably mounting the template on the bone comprises:
   a plurality of mounting holes formed on the template; and
   a plurality of fasteners, each fastener being adapted to pass through a corresponding one of the mounting holes and engage the bone.

25. The milling system as recited in claim 24, wherein the base comprises:
   an annular ring that encircles the opening; and
   at least three spaced apart hubs projecting from the annular ring into the opening, each hub having a corresponding one of the mounting holes extending therethrough.

26. The milling system as recited in claim 22, wherein the brace is pivotably mounted to the template.

27. The milling system as recited in claim 22, wherein the brace is slidably mounted to the template.

28. The milling system as recited in claim 22, further comprising a tubular sleeve having a passage extending therethrough, the mill being rotatably disposed within the tubular sleeve, the tubular sleeve being coupled with the brace.

29. The milling system as recited in claim 28, wherein:
   the template further comprises a bracket projecting from the base and extending along the length of the opening;
   the brace is movably mounted on the bracket; and
   the guide is coupled with and selectively movable along the length of the bracket, wherein the opening of the template, the brace, and the guide can be vertically aligned.

30. The milling system as recited in claim 29, further comprising a retainer movably coupling the tubular sleeve to the guide.

31. The milling system as recited in claim 22, wherein the brace and the guide allowing the mill to move in three dimensions so as to form a substantially continuous nonplanar resected surface on the bone.

32. A system for use in resecting at least a portion of a joint articulation surface of a bone, the system comprising:
   a mill comprising an elongated shaft having a burr mounted on an end thereof;
   a tubular sleeve having a passage extending therethrough, the mill being rotatably disposed within the tubular sleeve;
   a retainer having a passage extending therethrough, the tubular sleeve being at least partially disposed within the passage, the retainer being releasably lockable to the tubular sleeve at at least two spaced apart locations along the length of the tubular sleeve, the retainer being moved along the length of the tubular sleeve when the retainer is moved to lock with the tubular sleeve at each of the at least two spaced apart locations; and
   an elongated guide, the retainer being movably coupled with the guide so as to be movable in a direction substantially normal to the elongated shaft of the mill, the guide allowing the mill to move in three dimensions so as to form a substantially continuous non-planar resected surface on a bone.

33. The system as recited in claim 32, further comprising a bearing disposed within the tubular sleeve and encircling the mill.

34. The system as recited in claim 32, further comprising:
   a plurality of notches recessed on an exterior surface of the tubular sleeve, the plurality of notches being spaced longitudinally along the length of the tubular sleeve; and
   the retainer comprising at least one resiliently biased finger engaging with a select one of the plurality of notches.

35. The system as recited in claim 32, wherein the guide comprises a head and a pair of spaced apart arms projecting from the head.

36. The system as recited in claim 35, further comprising:
   a slot formed along the length of each arm of the guide; and
   a post projecting from each side of the retainer, the retainer being disposed between the arms of the guide with each post being slidably disposed within the slot of a corresponding arm.

37. The system as recited in claim 32, further comprising a template comprising a base having a top surface and an opposing bottom surface with an opening extending therebetween, the guide being movably mounted to the template and a portion of the mill being disposed within the opening of the template.

* * * * *